US008927528B2

(12) United States Patent
Miller et al.

(10) Patent No.: US 8,927,528 B2
(45) Date of Patent: *Jan. 6, 2015

(54) COMPOSITION FOR TREATING HEARING LOSS

(71) Applicant: The Regents of the University of Michigan, Ann Arbor, MI (US)

(72) Inventors: Josef Miller, Ann Arbor, MI (US); Colleen LePrell, Gainesville, FL (US); Jochen Schact, Ann Arbor, MI (US); Diane Prieskorn, Livonia, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 229 days.

This patent is subject to a terminal disclaimer.

(21) Appl. No.: 13/679,224

(22) Filed: Nov. 16, 2012

(65) Prior Publication Data

US 2013/0078320 A1     Mar. 28, 2013

Related U.S. Application Data

(63) Continuation-in-part of application No. 12/761,121, filed on Apr. 15, 2010, now Pat. No. 8,338,397, which is a continuation-in-part of application No. 11/623,888, filed on Jan. 17, 2007, now Pat. No. 7,951,845, application No. 13/679,224, which is a continuation-in-part of application No. 13/091,931, filed on Apr. 21, 2011, now Pat. No. 8,338,398, which is a continuation of application No. 11/623,888, filed on Jan. 17, 2007, now Pat. No. 7,951,845.

(60) Provisional application No. 60/760,055, filed on Jan. 19, 2006.

(51) Int. Cl.
| | |
|---|---|
| *A61K 33/06* | (2006.01) |
| *A61K 31/355* | (2006.01) |
| *A61K 31/60* | (2006.01) |
| *A61K 31/07* | (2006.01) |
| *A61K 31/375* | (2006.01) |
| *A61K 31/245* | (2006.01) |
| *A61K 31/7036* | (2006.01) |
| *A61K 31/015* | (2006.01) |
| *A61K 45/06* | (2006.01) |
| *A61K 33/00* | (2006.01) |
| *A61K 31/05* | (2006.01) |

(52) U.S. Cl.
CPC .............. *A61K 33/06* (2013.01); *A61K 31/7036* (2013.01); *A61K 31/015* (2013.01); *A61K 31/375* (2013.01); *A61K 31/355* (2013.01); *A61K 45/06* (2013.01); *A61K 33/00* (2013.01); *A61K 31/05* (2013.01)
USPC ........... 514/171; 514/458; 514/474; 514/725; 514/733; 424/682

(58) Field of Classification Search
USPC ........... 514/458, 474, 725, 733, 171; 424/682
See application file for complete search history.

(56) References Cited

U.S. PATENT DOCUMENTS

| | | |
|---|---|---|
| 5,597,585 A | 1/1997 | Williams et al. |
| 6,093,417 A | 7/2000 | Petrus |
| 6,177,434 B1 | 1/2001 | Kopke et al. |
| 6,265,386 B1 | 7/2001 | Campbell |
| 6,288,106 B1 | 9/2001 | Pearson et al. |
| 6,423,321 B2 | 7/2002 | Tobinick |
| 6,524,619 B2 | 2/2003 | Pearson et al. |
| 6,562,378 B1 | 5/2003 | Chandra |
| 6,649,621 B2 | 11/2003 | Kopke et al. |
| 6,660,297 B2 | 12/2003 | Bartels et al. |
| 6,815,434 B2 | 11/2004 | Kil et al. |
| 7,786,100 B2 | 8/2010 | Miller et al. |
| 7,951,845 B2 | 5/2011 | Miller et al. |
| 8,053,424 B2 | 11/2011 | Miller et al. |
| 8,338,397 B2 | 12/2012 | Miller |
| 8,338,398 B2 | 12/2012 | Miller et al. |
| 2002/0061870 A1 | 5/2002 | Pearson et al. |
| 2003/0191064 A1 | 10/2003 | Kopke |
| 2004/0033273 A1 | 2/2004 | Patwardhan et al. |
| 2004/0096524 A1 | 5/2004 | Nair et al. |
| 2004/0101560 A1 | 5/2004 | Sawchuk et al. |
| 2004/0224012 A1 | 11/2004 | Suvanprakorn et al. |
| 2004/0247570 A1 | 12/2004 | Miller et al. |

(Continued)

FOREIGN PATENT DOCUMENTS

| | | |
|---|---|---|
| EP | 1258243 | 11/2002 |
| WO | WO 98/56761 | 12/1998 |

(Continued)

OTHER PUBLICATIONS

Yamasoba, T., Nuttall, A. L., Harris, C., Raphael, Y., Miller, J. M. (1998). Role of glutathione in protection against noise-induced hearing loss. Brain Res. 784, 82-90.

(Continued)

*Primary Examiner* — Sreeni Padmanabhan
*Assistant Examiner* — Sahar Javanmard
(74) *Attorney, Agent, or Firm* — Howard & Howard Attorneys PLLC

(57) ABSTRACT

A composition to be administered to a mammal for treating hearing loss is disclosed herein. The composition consists essentially of a biologically effective amount of vitamin A, vitamin C, vitamin E, and a vasodilator comprising magnesium. The composition optionally includes a withanolide and/or resveratrol. The vitamin A, vitamin C, vitamin E, and the vasodilator comprising magnesium provides an additive effect that is equal to or greater than a sum of the effects of the individual components.

20 Claims, 6 Drawing Sheets

(56) References Cited

U.S. PATENT DOCUMENTS

2004/0258781 A1  12/2004  Nair et al.
2005/0013854 A1   1/2005  Mannino et al.
2005/0070607 A1   3/2005  Andrus et al.
2005/0107338 A1   5/2005  Seidman

FOREIGN PATENT DOCUMENTS

| WO | WO 01/84961    | 5/2001  |
|----|----------------|---------|
| WO | WO 03/030818   | 4/2003  |
| WO | WO 2004/000297 | 12/2003 |
| WO | WO 2004/016100 | 2/2004  |
| WO | WO 2004/037205 | 5/2004  |
| WO | WO 2004/050021 | 6/2004  |

OTHER PUBLICATIONS http://www.menieres.org/forums/NonCGI/Forum1/HTML/003686.html Constricted Blood Vessels, 1 Page.
International Search Report, International Application No. PCT/US 07/01422, Mar. 4, 2008, 2 pages.
K. Cryns et al., "A genotype-phenotype correlation for GJB2 (connexin 26) deafness", J Med Genet 2004; 41: 147-154.
Szabo et al., "A Novel Potassium Channel in Lymphocyte Mitochondria", The Journal of Biological Chemistry, vol. 280, No. 13, Apr. 1, 2005, pp. 12790-12798.
Etsuo Niki, "Action of ascorbic acid as a scavenger of active and stable oxygen radicals", Am J Clin Nutr 1991; 54: 1119S-24S.
Tsuchihashi et al., "Action of Beta-Carotene as an Antioxidant against Lipid Peroxidation", Archives of Biochemistry and Biophysics, vol. 323, No. 1, Oct. 20, 1995, pp. 137-147.
Aoshiba et al., "Acute cigarette smoke exposure induces apoptosis of alveolar macrophages", Am J Physiol Lung Cell Mol Physiol 281: L1392-L1401, 2001.
"A Randomized, Placebo-Controlled, Clinical Trial of High-Dose Supplementation With Vitamins C and E, Beta Carotene and Zinc for Age-Related Degeneration and Vision Loss", Arch Ophthalmol, Oct. 2001; 119(10): 1417-1436.
Andrew Forge et al., "Aminoglycoside Antibiotics", Audiol Neurootol 2000; 5:3-22.
Isao Inoue et al., "ATP-sensitive K+ channel in the mitochondrial inner membrane", Letters to Nature, vol. 352, Jul. 18, 1991, 244-247.
Roman A. Eliseev et al., "Bcl-2 and tBid proteins counter-regulate mitochondrial potassium transport", Biochimica et Biophysica Acta 1604 (2003) 1-5.
Xue Wang et al., "Bcl-XL disrupts death-inducing signal complex formation in plasma membrane induced by hypoxia/reoxygenation", The FASEB Journal, Research Communication, pp. 1826-1833.
Kulawiak et al., "BK channel openers inhibit ROS production of isolated rat brain mitochondria", Experimental Neurology 212 (2008) 543-547.
Siemen et al., "CA 2+ -Activated K Channel of the BK-Type in the Inner Mitochondrial Membrane of a Human Glioma Cell Line", Biochemical and Biophysical Research Communications, 257, 549-554 (1999).
Carnevali et al., "Cigarette smoke extract induced oxidative stress and apoptosis in human lung fibroblasts", Am J Physiol Lung Cell Mol Physiol 284: L955-L963, 2003.
Schafer et al., "Comparing Beta-Carotene, Vitamin E and Nitric Oxide as Membrane Antioxidants", Biol. Chem. vol. 383, pp. 671-681, Mar./Apr. 2002.
Kelsell et al., "Connexin 26 mutations in hereditary non-syndromic sensorineural deafness", Letters to Nature, vol. 387, May 1997, pp. 80-83.
Piwonska et al., "Differential Distribution of Ca 2+ -Activated Potassium Channel Beta 4 Subunit in Rat Brain: Immunolocalization in Neuronal Mitochondria", Neuroscience 153 (2008) 446-460.
Ohlemiller et al., "Early Elevation of Cochlear Reactive Oxygen Species following Noise Exposure", Audio! Neurootol 1999;4:229-236.
Le Prell et al., "Electromotile hearing: Acoustic tones mask psychophysical response to high-frequency electrical stimulation of intact guinea pig cochlea", J, Acoust. Soc. Am. 120 (6), Dec. 2006, pp. 3889-3900.
Nele Hilgert et al., "Forty-six genes causing nonsyndomic hearing impairment: Which ones should be analyzed in Dna diagnostics?", Mutation Research 681 (2009) pp. 189-196.
Kikuchi et al., "Gap junction systems in the mammalian cochlea", Brain Research Reviews 32 (2000), pp. 163-166.
Nickel et al., "Gap junctions and connexins in the inner ear: their roles in homeostasis and deafness", Current Opinion in Otolryngology & head and Neck Surgery 2008, 16:452-457.
Agustin D. Martinez et al., "Gap-Junction Channel Dysfunction in Deafness and Hearing Loss," Antioxidants & Redox Signaling, vol. 11, No. 2, 2009.
Ohinata et al., "Glutathione limits noise-induced hearing loss", Hearing Research 146 (2000) 28-34.
Wang et al., "Hepatocyte Growth Factor Protects against Hypoxia/Reoxygenation-induced Apoptosis in Endothelial Cells", The Journal of Biological Chemistry, vol. 279, No. 7, Feb. 13, 2004, pp. 5237-5243.
Budinger et al., "Hyperoxia-induced Apoptosis Does Not Require Mitochondrial Reactive Oxygen Species and Is Regulated by Bcl-2 Proteins", The Journal of Biological Chemistry, vol. 277, No. 18, May 3, 2002, pp. 15654-15660.
Yamasoba et al., "Influence of intense sound exposure on glutathione synthesis in the cochlea", Brain Research 804 (1998) 72-78.
Niki et al., "Interation among Vitamin C, Vitamin E, and Beta-Carotene ^ 1-3", Am J Clin Nutr 1995; 62(suppl): 1322S-6S.
Niki, "Interaction of Ascorbate and Alpha-Tocohpperol", Department of Reaction Chemistry, Faculty of Engineering, University of Tokyo, pp. 186-199.
Burton et al., "Is Vitamin E the Only Lipid-Soluble, Chain-Breaking Antioxidant in Human Blood Plasma and Erythrocyte Membranes?", Archives of Biochemistry and Biophysics, vol. 221, No. 1, Feb. 15, 1983, pp. 281-290.
Wangemann, "K+ Cycling and Its Regulation in the Cochlea and the Vestibular Labyrinth", Audiol Neurootol 2002; 7: 199-205.
Wangemann, "K+ Cycling and the endocochlear potential", Hearing Research 165 (2002) 1-9.
Niki, "Lipid antioxidants: How they may act in biological systems", Br. J. Cancer (1987), 55, Suppl. VIII, 153-157.
Ryter et al., "Comprehensive Invited Review: Mechanisms of Cell Death in Oxidative Stress", Antioxidants & Redox Signaling, vol. 9, No. 1, 2007, pp. 49-89.
Bednarczyk et al., "New Properties of mitochondrial ATP-regulated potassium channels", J. Bionerg Biomembr (2008), 40:325-335.
Morton et al., "Newborn Hearing Screening—A Silent Revolution", New Engl J Med 2006; 354:2151-64.
Altura et al., "Noise-induced hypertension and magnesium in rats: relationship to microcirculation and calcium", J Appl Physiol (1992), 72:194-202.
Rybak et al., "Ototoxicity", Kidney International (2007) 72, 931-935.
Ames et al., "Oxidants, antioxidants, and the degenerative diseases of aging", Proc. Natl. Acad. Sci. USA, Sep. 1993, vol. 90, pp. 7915-7922.
Zhao et al., "Oxidative damage pathways in relation to normal tissue injury", The British Journal of Radiology, 80 (2007), S23-S31.
Coyle et al., "Pendred syndrome (goitre and sensorineural hearing loss) maps to chromosome 7 in the region containing the nonsyndromic deafness gene DFNB4", Apr. 1996, Nature Genetics, vol. 12, pp. 421-423.
Hilgert et al., "Phenotypic variability of patients homozygous for the GJB2 mutation 35delG cannot be explained by the influence of one major modifier gene", European Journal of Human Genetics (2009) 17, pp. 517-524.
Agarwal et al., "Phospholipase Activation Triggers Apoptosis in Photosensitized Mouse Lymphoma Cells", Cancer Research 53, Dec. 15, 1993, pp. 5897-5902.
Scheibe et al., "Preventive magnesium supplement reduces ischemia-induced hearing loss and blood viscosity in the guinea pig", Eur Arch Otorhinolaryngol (2000) 257: 355-361.

(56) References Cited

OTHER PUBLICATIONS

Yu, "Regulation and critical role of potassium homeostasis in apoptosis", Progress in Neurobiology 70 (2003) pp. 363-386.

Soares et al., "Sequestering Ability of Butylated Hydroxytoluene, Propyl Gallate, Resveratrol, and Vitamins C and E against ABTS, DPPH, and Hydroxul Free Radicals in Chemical and Biological Systems", J. Agric. Food Chem. 2003, 51, 1077-1080.

Godar et al., "Spectral Dependence of UV-Induced Immediate and Delayed Apoptosis: The Role of Membrane and DNA Damage", Photochemistry and Photobiology, vol. 62, No. 1, pp. 108-113, 1995.

Wang et al., "Tanshinone (Salviae miltiorrhizae Extract) Preparations Attenuate Aminoglycoside-Induced Free Radical Formation in Vitro and Ototoxicity in Vivo", Antimicrobial Agents and Chemotherapy, Jun. 2003, vol. 47, No. 6, pp. 1836-1841.

Ahn et al., Anti-Apoptotic Role of Retinoic Acid in the Inner Ear of Noise-Exposed Mice, Biochemical and Biophysical Research Commmunications 335 (2005) 485-490.

Abaamrane et al., "Long-term Administration of Magnesium After Acoustic Trauma Caused by Gunshot Noise in Guinea Pigs", Hearing Research 247, 2009, pp. 137-145.

Attias, J., Bresloff, I., Haupt, H., Scheibe, F., Ising, H. (2003). "Preventing noise induced otoacoustic emission loss by increasing magnesium (Mg2+) intake in guinea-pigs." J. Basic Clin. Physiol. Pharmacol. 14, 119-136.

Attias, J., Weisz, G., Almog, S., Shahar, A., Wiener, M., Joachims, Z., Netzer, A., Ising, H., Rebentisch, E., Guenther, T. (1994). Oral magnesium intake reduces permanent hearing loss induced by noise exposure. Am. J. Otolaryngol. 15, 26-32.

Attias et al., "Reduction in Noise-Induced Temporary Threshold Shift in Humans Following Oral Magnesium Intake", Clinical Otolaryngology 29, Blackwell Publishing Ltd, 2004, pp. 635-641.

Balavoine GG, Geletii YV (1999) Peroxynitrite scavenging by different antioxidants. Part I: Convenient Assay. Nitric Oxide 3:40-54.

Bertolaso, L., Martini, A., Bindini, D., Lanzoni, I., Parmeggiani, A., Vitali, C., Kalinec, G., Kalinec, F., Capitani, S., Previati, M. (2001). Apoptosis in the OC-k3 immortalized cell line treated with different agents. Audiology 40, 327-35.

Biesalski, H. K., Wellner, U., Weiser, H. (1990). Vitamin A deficiency increases noise susceptibility in guinea pigs. J. Nutr. 120, 726-37.

Bock GR, Yakes GK, Miller JJ, Moorjani, P. "Effects of N-acetylcysteine on kanamycin ototoxicity in the guinea pig", Hear Res 9:255-262, 1983.

Boland A, Gerardy J, Mossay D, Seutin V (2003) Pre- and post-treatment with pirlindole and dehydropirlindole protects cultured brain cells against nitric oxide-induced death. Eur J Pharmacol 466:21-30.

Branis et al., "Effect of Ascorbic Acid on the Numerical Hair Cell Loss in Noise Exposed Guinea Pigs", Hearing Research 33, Elsevier Science Publishers B.V., 1988, pp. 137-140.

Cevette, M. J., Vormann, J., Franz, K. (2003). Magnesium and hearing. J. Am. Acad. Audiol. 14, 202-12.

Chae HJ, Chae SW, Reed JC, Kim HR (2004) Salicylate regulates COX-2 expression through ERK and subsequent NF-kappaB activation in osteoblasts. Immunopharmacol Immunotoxicol 26:75-91.

Diamond, B. J., Shiflett, S. C., Feiwel, N., Matheis, R. J., Noskin, O., Richards, J. A., Schoenberger, N. E. (2000). *Ginkgo biloba* extract: mechanisms and clinical indications. Arch. Phys. Med. Rehabil. 81, 668-78.

Didier, A., Droy-Lefaix, M. T., Aurousseau, C., Cazals, Y. (1996). Effects of *Ginkgo biloba* extract (EGb 761) on cochlear vasculature in the guinea pig: morphometric measurements and laser Doppler flowmetry. Eur. Arch. Otorhinolaryngol. 253, 25-30.

Duan, M., Qiu, J., Laurell, G., Olofsson, A., Counter, S. A., Borg, E. (2004). Dose and time-dependent protection of the antioxidant N-L-acetylcysteine against impulse noise trauma. Hear. Res. 192, 1-9.

Evans, P., Halliwell, B. (1999). Free radicals and hearing. Cause, consequence, and criteria. Ann. N. Y. Acad. Sci. 884, 19-40.

Fetoni AR, Sergi B, Ferraresi A, Paludetti G, Troiani D (2004) alpha-Tocopherol protective effects on gentamicin ototoxicity: an experimental study. Int J Audiol 43:166-171.

Fischer et al., "Protection of the Cochlea by Ascorbic Acid in Noise Trauma", HNO 57(4), Apr. 2009, pp. 339-344.

English language abstract for Fischer et al., "Protection of the Cochlea by Ascorbic Acid in Noise Trauma", HNO 57 (4), Apr. 2009, pp. 339-344.

Floyd RA (1999) Antioxidants, oxidative stress, and degenerative neurological disorders. Proc Soc Exp Biol Med 222:236-245.

Garetz SL, Rhee DJ, Schacht J, "Sulphydryl compounds and antioxidants inhibit cytotoxicity to outer hair cells of a gentamicin metabolite in vitro", Hear Res 77:75-80, 1994.

Gordin, A., Goldenberg, D., Golz, A., Netzer, A., Joachims, H. Z. (2002). Magnesium: a new therapy for idiopathic sudden sensorineural hearing loss. Otol. Neurotol. 23, 447-51.

Gunther, T., Ising, H., Joachims, Z. (1989). Biochemical mechanisms affecting susceptibility to noise-induced hearing loss. Am. J. Otol. 10, 36-41.

Gutteridge, J. M. C., Halliwell, B. 1999. Antioxidant protection and oxygen radical signaling. In: Gilbert, D.L., Colton, C. A., (Eds.), Reactive oxygen species in biological systems: an interdisciplinary approach. Kluwer Academic/Plenum Publishers, NewYork. pp. 189-218.

Halliwell, B, Gutteridge, J.M.C., Free Radicals in Biology and Medicine, 3rd Ed., Oxford Univ. Press (1999), Chapter 3—Antioxidant defences, pp. 105-245.

Haupt, H. Scheibe, F. (2002). Preventive magnesium supplement protects the inner ear against noise-induced impairment of blood flow and oxygenation in the guinea pig. Magnes. Res. 15, 17-25.

Haupt, H., Scheibe, F., Mazurek, B. (2003). Therapeutic efficacy of magnesium in acoustic trauma in the guinea pig. ORL. J. Otorhinolaryngol. Relat. Spec. 65, 134-9.

Heinrich et al, "Ascorbic Acid Reduces Noise-Induced Nitric Oxide Production in the Guinea Pig Ear", Laryngoscope 118, The American Laryngological, Rhinological and Otological Society, Inc., May 2008, pp. 837-842.

Henderson, D., McFadden, S. L., Liu, C. C., Hight, N., Zheng, X. Y. (1999). The role of antioxidants in protection from impulse noise. Ann. N. Y. Acad. Sci. 884, 368-80.

Hight, N. G., McFadden, S. L., Henderson, D., Burkard, R. F., Nicotera, T. (2003). Noise-induced hearing loss in chinchillas pre-treated with glutathione monoethylester and R-PIA. Hear. Res. 179, 21-32.

Hoffman DW, Jones-King KL, Whitworth CA, Rybak LP, "Potentiation of ototoxicity by glutathione depletion", Ann Ototol Rhinol Laryngol 97(1):36-41, 1988.

Hou, F., Wang, S., Zhai, S., Hu, Y., Yang, W., He, L. (2003). Effects of alpha-tocopherol on noise-induced hearing loss in guinea pigs. Hear. Res. 179, 1-8.

Hu, B. H., Zheng, X. Y., McFadden, S. L., Kopke, R. D., Henderson, D. (1997). R-phenylisopropyladenosine attenuates noise-induced hearing loss in the chinchilla. Hear. Res. 113, 198-206.

Ising, H., Handrock, M., Gunther, T., Fischer, R., Dombrowski, M. (1982). Increased noise trauma in guinea pigs through magnesium deficiency. Arch. Otorhinolaryngol. 236, 139-46.

Jackson, R. L., Coleman, J. K, Ge, X., Liu, J., Hoffer, M. E., Balough, B. (2005). Antioxidant strategies for post-noise hearing loss recovery, International Symposium—Pharmacologic Strategies for Prevention and Treatment of Hearing Loss and Tinnitus, Niagra Falls, Ottawa, Canada, one page.

Jacono A.A., Hu B, Kopke RD, Henderson D, Van De Water TR, Steinman HM (1998) Changes in cochlear antioxidant enzyme activity after sound conditioning and noise exposure in the chinchilla. Hear Res 117:31-38.

Joachims, H. Z., Segal, J., Golz, A., Netzer, A., Goldenberg, D. (2003). Antioxidants in treatment of idiopathic sudden hearing loss. Otol. Neurotol. 24, 572-5.

Joachims, Z., Babisch, W., Ising, H., Gunther, T., Handrock, M. (1983). Dependence of noise-induced hearing loss upon perilymph magnesium concentration. J. Acoust. Soc. Am. 74, 104-8.

Joachims, Z., Netzer, A., Ising, H., Rebentisch, E., Attias, J., Weisz, G., Gunther, T. (1993). Oral magnesium supplementation as prophylaxis for noise-induced hearing loss: results of a double blind field study. Schriftenr. Ver. Wasser. Boden. Lufthyg. 88, 511-516.

(56) References Cited

OTHER PUBLICATIONS

Jung, H. W., Chang, S. O., Kim, C. S., Rhee, C. S., Lim, D. H. (1998). Effects of *Ginkgo biloba* extract on the cochlear damage induced by local gentamicin installation in guinea pigs. J. Korean Med. Sci. 13, 525-8.
Kalkanis, J. G., Whitworth, C., Rybak, L. P. (2004). Vitamin E reduces cisplatin ototoxicity. Laryngoscope 114, 538-42.
Knight, W. 2002. Popping pill may prevent hearing loss [Online] http://www.newscientist.com/article.ns?id=dn2666 (posted Aug. 13, 2002; verified Feb. 25, 2005) on 2 pages.
Kopke, R. D. (2005). NAC for Noise: From the bench top to the clinic, International Symposium—Pharmacologic Strategies for Prevention and Treatment of Hearing Loss and Tinnitus, Niagara Falls, Ottawa, Canada, one page.
Kopke, R. D., Coleman, J. K., Liu, J., Campbell, K. C., Riffenburgh, R. H. (2002). Candidate's thesis: Enhancing intrinsic cochlear stress defenses to reduce noise-induced hearing loss. Laryngoscope 112, 1515-32.
Kopke, R. D., Weisskopf, P. A., Boone, J. L., Jackson, R. L., Wester, D. C., Hoffer, M. E., Lambert, D. C., Charon, C. C., Ding, D. L., McBride, D. (2000). Reduction of noise-induced hearing loss using L-NAC and salicylate in the chinchilla. Hear. Res. 149, 138-46.
Kopke R, Allen KA, Henderson D, Hoffer M, Frenz D, Van de Water T(1999) A radical demise. Toxins and trauma share common pathways in hair cell death. Ann N Y Acad Sci 884:171-191.
Kujawa S.G., Liberman M.C., Acceleration of Age-Related Hearing Loss by Early Noise Exposure: Evidence of a Misspent Youth, Journal of Neuro., (Feb. 15, 2006—26(7): 2115-2123.
Kujawa, S. (2005). Adding insult to injury: Noise-induced and age-related hearing loss interactions, International Symposium—Pharmacologic Strategies for Prevention and Treatment of Hearing Loss and Tinnitus, Niagra Falls, Ottawa, Canada, one page.
Kwon KS, Chae HJ (2003) Sodium salicylate inhibits expression of COX-2 through suppression of ERK and subsequent NF-kappaB activation in rat ventricular cardiomyocytes. Arch Pharm Res 26:545-553.
Laurikainen et al., "Betahistine Effects on Cochlear Blood Flow: From the Laboratory to the Clinic", Acta Otolaryngol, Supp. 544, 2000, pp. 5-7.
Laurikainen et al., "Non-Specific Effect of Beettahistine on Cochlear Electrophysiology in Guinea Pig", Acta Otolayngol (Stockh), Supp. 529, 1997, pp. 77-79.
Lautermann J, McLaren J, Schacht J, "Glutathione protection against gentamicin ototoxicity depends on nutritional status", Hear Res 86:15-24, 1995.
Le Prell et al., "Free Radical Scavengers Vitamins A, C and E Plus Magnesium Reduce Noise Trauma", Free Radical Biology & Medicine 42, 2007, pp. 1454-1463.
Le Prell et al., "Mechanisms of Noise-Induced Hearing Loss Indicate Multiple Methods of Prevention", Hearing Research 226, Elsevier B.V., 2007, pp. 22-43.
Le Prell CG, Dolan DF, Schacht J, Miller JM, Lomax MI, Altschuler RA (2003) Pathways for protection from noise induced hearing loss. Noise Health 5:1-17.
Li G, Sha SH, Zotova E, Arezzo J, Van de Water T, Schacht J (2002) Salicylate protects hearing and kidney function from cisplatin toxicity without compromising its oncolytic action. Lab Invest 82:585-596.
Lohle, E. (1980). The influence of a chronic vitamin A deficiency on the acoustic sensory cells and the ganglion spirale cochleae of the rat. An electron microscope study. Arch. Otorhinolaryngol. 229, 45-53.
Lohle, E. (1985). Ultrastructural changes in the organ of Corti and in the ganglion spiral cochleae after vitamin A deficiency. Pathol. Res. Pract. 179, 560-7.
Lopez-Gonzalez, M. A., Guerrero, J. M., Rojas, F., Delgado, F. (2000). Ototoxicity caused by cisplatin is ameliorated by melatonin and other antioxidants. J. Pineal Res. 28, 73-80.
McFadden, S.L., Wo, J.M., Michalak, N. Ding D., Dietary Vitamin C Supplementation Reduces Noise-Induced Hearing Loss in Guinea Pigs, Hearing Research 202 (2005) 200-208.

Miller et al., "Interactive Effects of Aging with Noise Induced Hearing Loss", Scand. Audiol, 27, 1998, pp. 53-61.
Miller et al., "Mechanisms and Prevention of Noise-Induced Hearling Loss", Otol Jpn, 16(2): 2006, pp. 139-1.
Miller, J. M., Brown, J. N., Schacht, J. (2003). 8-iso-prostaglandin F(2alpha), a product of noise exposure, reduces inner ear blood flow. Audiol. Neurootol. 8, 207-21.
Minami et al., "Creatine and Tempol Attenuate Noise-Induced Hearing Loss", Brain Res. May 7, 2007, pp. 1-13.
Nageris, B. I., Ulanovski, D., Attias, J. (2004). Magnesium treatment for sudden hearing loss. Ann. Otol. Rhinol. Laryngol. 113, 672-5.
Ohinata, Y., Miller, J. M., Schacht, J. (2003). Protection from noise-induced lipid peroxidation and hair cell loss in the cochlea. Brain Res. 966, 265-73.
Ohinata, Y., Miller, J. M., Altschuler, R. A., Schacht, J. (2000a). Intense noise induces formation of vasoactive lipid peroxidation products in the cochlea. Brain Res. 878, 163-73.
Ohinata, Y., Yamasoba, T., Schacht, J., Miller, J. M. (2000b). Glutathione limits noise-induced hearing loss. Hear. Res. 146, 28-34.
Omenn, G. S., Goodman, G. E., Thornquist, M. D., Balmes, J., Cullen, M. R., Glass, A., Keogh, J. P., Meyskens, F. L., Valanis, B., Williams, J. H., Barnhart, S., Hammar, S. (1996). Effects of a combination of beta carotene and vitamin A on lung cancer and cardiovascular disease. N. Engl. J. Med. 334, 1150-5.
Perlman, H. B., Kimura, R. (1962). Cochlear blood flow and acoustic trauma. Acta Otolaryngol. (Stockh). 54, 99-119.
Pierson MG, Moller AR, "Prophylaxis of kanamycin-induced ototoxicity by a radioprotectant", Hear Res 4:79-87, 1981.
Priuska EM, Schacht J, "Formation of free radicals by gentamicin and iron and evidence for an iron-gentamicin complex", Biochem Pharmacol 50(11):1749-1752, 1995.
Rabinowitz, P. M., Pierce Wise, J., Sr., Hur Mobo, B., Antonucci, P. G., Powell, C., Slade, M. (2002). Antioxidant status and hearing function in noise-exposed workers. Hear. Res. 173, 164-71.
Romeo, G. (1985) The Therapeutic Effect of Vitamins A and E in Neurosensory Hearing Loss, [Italian] Journal Article—Acta Vitamininol. Enzymol. 7 Suppl:85-92, One Page English Abstract from OVID Search Results.
Schacht, J. (1999). Antioxidant therapy attenuates aminoglycoside-induced hearing loss. Ann. N. Y. Acad. Sci. 884, 125-30.
Scheibe, F., Haupt, H., Ising, H. (1999). Total magnesium concentrations of perilymph, cerebrospinal fluid and blood in guinea pigs fed different magnesium-containing diets. Eur. Arch. Otorhinolaryngol. 256, 215-9.
Scheibe, F., Haupt, H., Ising, H. (2000). Preventive effect of magnesium supplement on noise-induced hearing loss in the guinea pig. Eur. Arch. Otorhinolaryngol. 257, 10-16.
Scheibe, F., Haupt, H., Ising, H., Cherny, L. (2002). Therapeutic effect of parenteral magnesium on noise-induced hearing loss in the guinea pig. Magnes. Res. 15, 27-36.
Schneider, D., Schneider, L., Shulman, A., Claussen, C. F., Just, E., Koltchev, C., Kersebaum, M., Dehler, R., Goldstein, B., Claussen, E. (2000). *Gingko biloba* (Rokan) therapy in tinnitus patients and measurable interactions between tinnitus and vestibular disturbances. Int. Tinnitus J. 6, 56-62.
Seidman, M., Babu, S., Tang, W., Naem, E., Quirk, W. S. (2003). Effects of resveratrol on acoustic trauma. Otolaryngol. Head Neck Surg. 129, 463-70.
Seidman, M. D. (2000). Effects of dietary restriction and antioxidants on presbyacusis. Laryngoscope 110, 727-38.
Sergi, B., Fetoni, A.R., Ferraresi, A., Troiani, D., Azzena, G.B., Paludetti, G., Maurizi, M. (2004). The role of antioxidants in protection from ototoxic drugs. Acta Otolaryngol. Suppl. (Stockh). 42-5.
Sha SH, Schacht J (1999) Salicylate attenuates gentamicin-induced ototoxicity. Lab Invest 79:807-813.
Sha SH, Qiu JH, Schacht J, "Aspirin to prevent gentamicin-induced hearing loss", N. Engl J Med 354(17):1856-7, 2006.
Sha SH, Schacht J, "Formation of reactive oxygen species following bioactivation of gentamicin", Free Rad Biol Med 26(3-4):341-347, 1999.
Shoji et al., "Differential Protective Effects of Neurotrophins in the Attenuation of Noise-Induced Hair Cell Loss", Hearing Research 146, 2000, pp. 134-142.

(56) References Cited

OTHER PUBLICATIONS

Song, B.-B., Sha, S. H., Schacht, J. (1998). Iron chelators protect from aminoglycosideinduced cochleo- and vestibulotoxicity in guinea pig. Free Radic. Biol. Med. 25, 189-195.

Song B-B, Schacht J, "Variable efficacy of radical scavengers and iron chelators to attenuate gentamicin ototoxicity in guinea pig in vivo", Hear Res 94:87-93, 1996.

Takemura et al., "Direct Inner Ear Infusion of Dexamethasone Attenuates Noise-Induced Trauma in Guinea Pig", Hearing Research 196, 2004, pp. 58-68.

Takumida, M., Anniko, M., Ohtani, M. (2003). Radical scavengers for Meniere's disease after failure of conventional therapy: a pilot study. Acta Otolaryngol. (Stockh). 123, 697-703.

Tanswell AK, Freeman BA (1995) Antioxidant therapy in critical care medicine. New Horizons 3:330-341. One page abstract from OVID:Search Results on Apr. 22, 2006.

Teranishi, M., Nakashima, T., Wakabayashi, T. (2001). Effects of alpha-tocopherol on cisplatin-induced ototoxicity in guinea pigs. Hear. Res. 151, 61-70.

The Alpha-Tocopherol, Beta Carotene Cancer Prevention Study Group. (1994). The effect of vitamin E and beta carotene on the incidence of lung cancer and other cancers in male smokers. N. Engl. J. Med. 330, 1029-1035.

Usami, S., Hjelle, O. P., Ottersen, O. P. (1996). Differential cellular distribution of glutathione—an endogenous antioxidant—in the guinea pig inner ear. Brain Res. 743, 337-40.

Watanabe, K., Inai, S., Hess, A., Michel, O., Yagi, T. (2004). Acoustic stimulation promotes the expression of inducible nitric oxide synthase in the vestibule of guinea pigs. Acta Otolaryngol. Suppl. 553: (Stockh). 54-57.

Weijl, N. I., Elsendoorn, T. J., Lentjes, E. G., Hopman, G. D., Wipkink-Bakker, A., Zwinderman, A. H., Cleton, F. J., Osanto, S. (2004). Supplementation with antioxidant micronutrients and chemotherapy-induced toxicity in cancer patients treated with cisplatin-based chemotherapy: a randomised, double-blind, placebo-controlled study. Eur. J. Cancer 40, 1713-1723.

Yamashita, D., Jiang, H.-Y., Le Prell, C. G., Schacht, J., Miller, J. M. (2005). Post-exposure treatment attenuates noise-induced hearing loss. Neuroscience, 134, 633-642.

Yamashita D, Jiang HY, Schacht J, Miller JM (2004) Delayed production of free radicals following noise exposure. Brain Res 1019: 201-209.

Yamasoba et al., "Attenuation of Cochlear Damage From Noise Trauma by an Iron Chelator, a Free Radical Scavenger and Glial Cell Line-Derived Neurotrophic Factor in Vivo", Brain Research 815, 1999, pp. 317-325.

Cohen-Salmon et al., "Targeting Ablation of Connexin26 in the Inner Ear Epithelial Gap Junction Network Causes Hearing Impairment and Cell Death", Current Biology, vol. 12, Jul. 9, 2002, pp. 1106-1111.

Oleinick et al., "The Photobiology of Photodynamic Therapy: Cellular Targets and Mechanisms", Radiation Research 150 (Suppl.), S146-S156 (1998).

Godar, "UVA1 Radiation Triggers Two Different Final Apoptotic Pathways", 1999, The Society fir Investigative Dermatology Inc., pp. 3-12.

Chan DK, Schrijver I, Chang KW. Connexin-26-associated deafness: phenotypic variability and progression of hearing loss. Genet Med. 2010;12:174-81.

Green GE, Smith RJ, Bent JP, Cohn ES. Genetic testing to identify deaf newborns. JAMA. 2000;284:1245.

Green GE, Mueller RF, Cohn ES, Avraham KB, Kanaan M, Smith RJH. Audiological Manifestations and Features of Connexin 26 Deafness. Aud Med. 2003;1:5-11.

Kenna MA, Feldman HA, Neault MW, Frangulov A, Wu BL, Fligor B. Rehm HL. Audiologic phenotype and progression in GJB2 (Connexin 26) hearing loss. Arch Otolaryngol Head Neck Surg. Jan. 2010;136(1):81-7.

Altura BH, Altura BM. Role of Mg ions in contractility of blood vessels and skeletal muscles. Magnesium-B 1a:102-114, 1981.

Glenn Green, Colleen Le Prell, and Josef Miller, Presentation, "Hearing Improvement on a CEMg in a Child with Connexin 26 Hearing Loss." Feb. 2011, (University of Michigan, University of Florida).

COMPOSITION FOR TREATING HEARING LOSS

RELATED APPLICATIONS

This patent application is a continuation-in-part of U.S. application Ser. No. 12/761,121 filed on Apr. 15, 2010, which is a continuation-in-part of U.S. application Ser. No. 11/623,888, filed on Jan. 17, 2007. U.S. application Ser. No. 11/623,888 is now U.S. Pat. No. 7,951,845, and U.S. application Ser. No. 11/623,888 claims priority to and all advantages of U.S. Provisional Patent App. Ser. No. 60/760,055, which was filed on Jan. 19, 2006. This patent application is also a continuation-in-part of U.S. application Ser. No. 13/091,931 filed on Apr. 21, 2011, which is a continuation of U.S. application Ser. No. 11/623,888 filed on Jan. 17, 2007. U.S. application Ser. No. 11/623,888 is now U.S. Pat. No. 7,951,845, and U.S. application Ser. No. 11/623,888 claims priority to and all advantages of U.S. Provisional Patent App. Ser. No. 60/760,055 filed on Jan. 19, 2006.

GOVERNMENT LICENSE RIGHTS

This invention was made with government support under DC004058 awarded by the National Institutes of Health. The government has certain rights in the invention.

BACKGROUND OF THE INVENTION

1. Field of the Invention

The present invention generally relates to a composition for treating hearing loss. More specifically, the composition includes components that provide an additive effect that is equal to or greater than the sum of the effects of the individual components.

2. Description of the Related Art

Extensive studies have been performed on compositions for treating side effects to antibiotic treatment, along with methods of treating the side effects using various compositions. Particularly problematic side effects from antibiotic treatment include kidney damage, loss of balance, and hearing loss attributable to antibiotic treatment such as aminoglycoside or glycopeptide antibiotic treatments. The damaging side effects of many aminoglycoside antibiotics were first reported in the 1940s, and the damaging side effects have long been an impediment to use of aminoglycoside antibiotics. Aminoglycoside antibiotics cause permanent deficits in the vestibular system (balance) and irreversible cell death in the cochlea, resulting in hearing impairment.

While the damaging side effects of aminoglycoside antibiotics, in particular, have impeded their use, it has not eliminated their use. Aminoglycoside antibiotics are the only "standard of treatment" in certain severe gram-negative bacterial infections, and the only inexpensive antibiotics that are available in developing countries. In the USA and European countries where the side effects are well recognized, and where $2^{nd}$ and $3^{rd}$ generation antibiotics are substituted wherever possible, side effects such as inner ear damage and hearing loss in patients can be minimized through careful monitoring of aminoglycoside antibiotic treatment. However, in countries in which there are fewer alternative drugs and monitoring is less rigorous or non-existent, side effects associated with aminoglycoside antibiotic treatment is more prevalent.

Notably, HIV death is often driven by tuberculosis as a secondary infection to HIV. In developing countries, aminoglycoside antibiotic treatment is widely used against tuberculosis. Given the generally lax monitoring and the high incidence of side effects associated with aminoglycoside antibiotic treatment in developing countries, poor patient compliance in completing proscribed aminoglycoside antibiotic treatment is common, contributing to the development of drug-resistant strains of tuberculosis.

Historically, from the first identification of side effects such as hearing loss attributable to aminoglycoside antibiotic treatment in the 1940s, research focused on identification of the aminoglycoside-induced pathophysiology and otohistopathology, the pharmacokinetics of the aminoglycoside antibiotics, and methods of monitoring early damage and thereby avoiding serious side effects attributable to aminoglycoside antibiotic treatment in humans. Mechanistic studies of aminoglycoside ototoxicity began in the 1980s. Findings that free-radical formation played a role in aminoglycoside ototoxicity were first indicated by reports of efficacy of some free radical scavengers in reducing ototoxicity. More direct evidence was uncovered in the mid to late 1990s of free radical formation by gentamicin (which is one type of aminoglycoside antibiotic), while ototoxicity attributable to aminoglycoside treatment was found to be inversely related to glutathione levels (endogenous antioxidant) in inner ear tissues. It has since been shown that ototoxicity of aminoglycoside antibiotics could be reduced by treatment with some radical scavengers.

Free radical formation has been shown to play a role in many instances of stress-induced cell pathology. High intensity noise has been shown to induce free radical formation. For the inner ear, the mechanism by which high intensity noise induces cell death in the cochlea and hearing impairment has been shown to be dependent on free radical formation. Noise-induced trauma to the inner ear has been shown to be inversely related to endogenous levels of glutathione in cochlear tissues.

The parallels between the mechanisms of noise- and antibiotic-induced cell death in the inner ear suggest that they share a common cell death pathway such that it is natural to speculate that agents found effective to attenuate noise-induced hearing loss may be effective to attenuate antibiotic-induced hearing loss. However, it is clear from the literature that great variability is found in the efficacy of some of the agents to reduce the damaging side effects of aminoglycoside antibiotics. To some extent, the variable efficacy may reflect differential mechanisms of action of the scavengers or unique molecular structures of the free radicals formed. Some agents have been tested for efficacy against noise-induced hearing loss (NIHL) and their relative efficacy has been found to differ from their relative efficacy for drug-induced hearing loss. For example, allopurinol is ineffective in reducing gentamicin-induced ototoxicity, but is effective in reducing noise-induced hearing loss. Given such observations (and other similar ones in literature), there is no substantial basis for believing that a formulation for treating noise-induced hearing loss will be effective to treat antibiotic-induced hearing loss and other side effects of antibiotic treatment.

In view of the foregoing, there remains further opportunities to develop effective methods of treating side effects of antibiotic treatment, including antibiotic-induced hearing loss, kidney damage, and loss of balance, the methods including the step of administering a composition that includes a specific combination of components, in biologically effective amounts, in conjunction with administration of antibiotics that are capable of causing side effects such as hearing loss in mammals.

There is also an opportunity to provide a composition and a method of treating hearing loss including the step of administering the composition that includes a specific combination of components having an additive effect that is equal to or greater than the sum of the effect of the individual components in treating hearing loss when used in biologically effective amounts.

SUMMARY OF THE INVENTION

The subject invention provides a composition to be administered to a mammal for treating hearing loss. The composition consists essentially of biologically effect amounts of vitamin A, vitamin E, vitamin C, a vasodilator comprising magnesium, and, optionally, a with anolid and/or resveratrol, to provide an additive effect that is equal to or greater than a sum of the effects of the individual components.

BRIEF DESCRIPTION OF THE DRAWINGS

Other advantages of the present invention will be readily appreciated, as the same becomes better understood by reference to the following detailed description when considered in connection with the accompanying drawings wherein.

DETAILED DESCRIPTION

Figure 1:
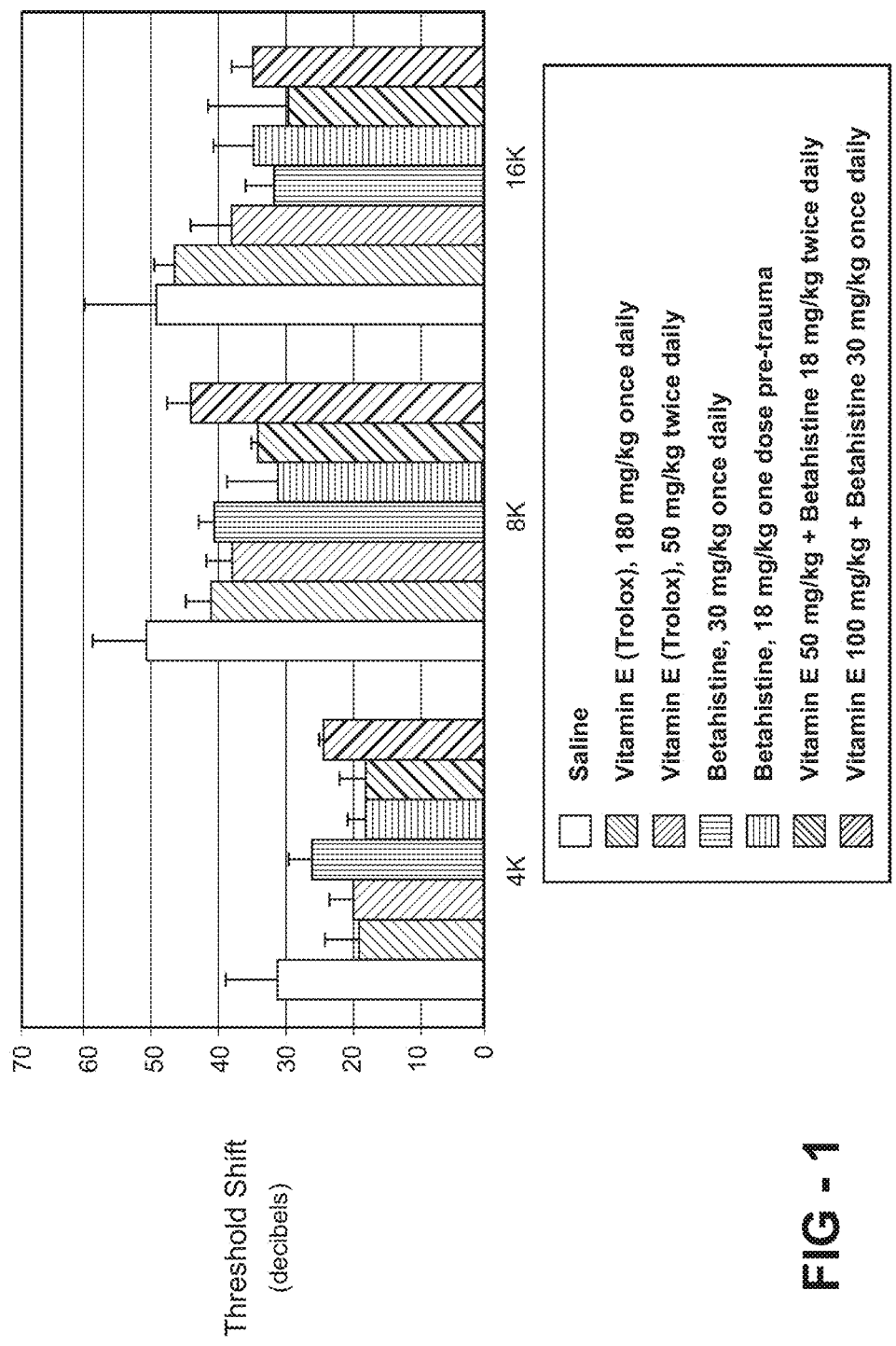
FIG. 1 is a graph showing the effect of a Comparative Example of a composition used to treat hearing loss including Trolox® (vitamin E) and betahistine on reduction of a threshold shift in guinea pigs from baseline threshold sensitivity at 4, 8, and 16 kHz after exposure to 120 decibel SPL Octave Band Noise centered at 4 kHz for five hours.

A composition for treating hearing loss includes components that may function through different biological mechanisms to provide an additive effect that is equal to or greater than a sum of the effect of the individual components. The composition is typically used for treating hearing loss resulting from trauma to an inner ear of a mammal. The trauma may be further defined as mechanically-induced metabolic trauma, mechanical/metabolic trauma, stress trauma, stress-induced damage, or environmental stress. However, it is also possible that the composition may also be used to treat or prevent other types of hearing loss, including, for example, age-related hearing loss, antibiotic-induced hearing loss, and chemotherapeutic-induced hearing loss. The composition may further be used to prevent hearing loss during restoration surgery performed on the inner ear.

Further, a method in accordance with the instant invention includes the step of administering a composition to a mammal that includes components that function through different biological mechanisms. The composition is typically used for treating hearing loss resulting from trauma to the inner ear of a mammal. However, as described in further detail below, the composition can be administered in conjunction with administration of an antibiotic and can be used to treat various side effects of the antibiotic treatment. The trauma to the inner ear of the mammal may be further defined as mechanically-induced metabolic trauma, mechanical/metabolic trauma, stress trauma, stress-induced damage, or environmental stress. In the context of the instant invention, the composition is used to treat or prevent side effects of antibiotic treatment including antibiotic-induced hearing loss. The composition may further be used to prevent hearing loss during restoration surgery performed on the inner ear.

It has been found that one result of noise trauma, or other stressors such as age and drugs such as antibiotics as set forth above, is that free radicals form in association with metabolic trauma. The free radicals damage sensitive structures, such as hair cells, within the ear. Vasoconstriction also occurs as a result of the noise, which leads to decreased blood flow to the inner ear and causes cell death that results in hearing loss. It has been found that the underlying cause of vasoconstriction is noise-induced free radical formation. Specifically, one of the molecules formed in the inner ear as a result of the presence of free radicals is 8-isoprostane-2F alpha, which is a bioactive agent. The bioactive agent induces a constriction of blood vessels in the inner ear, which causes a reduction in blood flow. In order to counteract the free radical formation and the vasoconstriction, the composition of the subject invention includes at least one scavenger of singlet oxygen, a donor antioxidant, a third antioxidant, and a vasodilator. Unexpectedly, it was found that the composition including the at least one scavenger of singlet oxygen, the donor antioxidant, the third antioxidant, and the vasodilator produce an additive effect that is not only greater than the effect of any one of those components alone, but at least equal to or greater than a sum of the effects of each of the components when used to treat noise-induced hearing loss. Similar effectiveness has also been found when the composition is used to treat side effects of antibiotic treatment including antibiotic-induced hearing loss.

Antioxidants act through a variety of mechanisms. The at least one scavenger of singlet oxygen and the donor antioxidant are two different classes of antioxidants that act through different mechanisms. The third antioxidant, while typically a scavenger of singlet oxygen, may be a different antioxidant that acts through a different mechanism. Scavengers of singlet oxygen reduce free radicals that contribute to hearing loss and other side effects of antibiotic treatment such as kidney damage and loss of balance. More specifically, by reducing free radicals, the scavengers of singlet oxygen prevent, among other damaging effects, the singlet oxygen from reacting with lipids to form lipid hydroperoxides. Lipid hydroperoxides play a role in causing hearing loss.

Even within the class of scavengers of singlet oxygen, it is believed that various antioxidants react at different sites within the body, and in particular, within cells to attenuate free radical formation. For example, one of the scavengers of singlet oxygen is typically vitamin A. Vitamin A is a generic term that captures a number of molecules with a biological activity of retinol or carotenoids. Primary dietary forms of vitamin A/retinol include retinol esters and beta-carotene. The beta-carotene is made up of a polyene chain of 11 conjugated double bonds with methyl branches spaced along the polyene chain, capped at both ends by cyclohexenyl rings with 1,1,5-trimethyl substitution. Other forms of vitamin A include xanxthophylls, astaxanthin, canthxanxin, lutein, and zeaxanthin, which include a backbone of beta-carotene with hydroxyl and/or carbonyl substitution on one or more of the cyclohexenyl rings. For purposes of the subject invention, the vitamin A is typically present as beta-carotene. Beta-carotene is a powerful scavenger of singlet oxygen, as well as nitric oxide and peroxynitrite, and may also scavenge lipid peroxyl radicals within a lipophilic compartment of a mitochondrial membrane. Beta-carotene is an excellent scavenger of free radicals under normal physiological conditions present in most tissues.

In addition to vitamin A, other scavengers of singlet oxygen may also be present in the composition of the subject invention. For example, another scavenger of singlet oxygen that may be present is resveratrol. Resveratrol is more efficient at scavenging hydroxyl radicals than vitamin C, and the addition of resveratrol to the vitamins A may have additive effects. The use of resveratrol in combination with other antioxidants (but not vitamins A, C, or E, and not the vasodilator magnesium or any other vasodilating substance), is known in the art to reduce age-related hearing loss.

The at least one scavenger of singlet oxygen is present in the composition in a biologically effective amount. For purposes of the subject invention, the biologically effective amount is further defined as an amount that is sufficient to produce an additive effect in a reduction in threshold shift when used in combination with other antioxidants and the magnesium. Additive effect, as used herein, refers to an effect that is equal to or greater than a sum of the effects of the individual components. In order to produce additive effect and the reduction in threshold shift, the at least one scavenger of singlet oxygen is typically present in the composition in a total amount of at least 830 international units (IU), more typically from 830 to 120,000 IU, most typically from about 2,100 to 70,000 IU for an adult dosage.

The amount of the vitamin A present in the composition is dependent upon the form of vitamin A that is used. For example, in one embodiment, vitamin A is present as retinol in an amount of at least 830 IU, more typically from 830 to 10,000 IU, more typically from 2,100 to 10,000 IU, most typically from 2,100 to 8,000 IU. As known in the art, a conversion of IU to weight for vitamin A (as retinol) is 3.33 IU/µg. Thus, at least 830 international units (IU) of vitamin A (as retinol) is equivalent to at least 0.25 mg of vitamin A, from 830 to 10,000 IU of vitamin A (as retinol) is equivalent to from 0.25 to 3 mg of vitamin A, and from 2,100 to 8,000 IU of vitamin A (as retinol) is equivalent to from 0.63 to 2.4 mg vitamin A.

Alternatively, the vitamin A may be present in the composition as beta-carotene, as opposed to retinol. The retinol activity equivalents (RAE) for retinol conversion to beta-carotene, which is a pro-vitamin A carotenoid, is 1 mg to 12 mg. In terms of conversion of the amounts set forth above for the vitamin A present in the composition as retinol to the vitamin A present in the composition as beta-carotene, in one example, a total amount of at least 3.0 mg or at least 830 international units (IU) of vitamin A as beta-carotene, more typically from 3.0 to 180 mg or 830 to 50,000 IU vitamin A as beta-carotene, most typically from about 7.2 to 108 mg or 2000 to 30,000 IU of vitamin A as beta-carotene is typically present for an adult dosage. In another example, a total amount of at least 3.0 mg or at least 10,000 international units (IU) of vitamin A as beta-carotene, more typically from 3.0 to 36 mg or 10,000 to 120,000 IU vitamin A as beta-carotene, most typically from about 7.5 to 21 mg or 25,000 to 70,000 IU of vitamin A as beta-carotene is typically present for an adult dosage.

Specific amounts of the vitamin A present in the composition may be dependent on the body weight of the mammal. In one specific example, the amount of vitamin A present as retinol in the composition is about 0.0178 mg/kg body weight. Thus, for an average human weighing about 70 kg, the amount of vitamin A present as retinol in the composition may be about 1.25 mg. If the vitamin A is in the form of beta-carotene, in one example, the beta carotene in the composition is about 0.257 mg/kg body weight may be present in an amount of about 18 mg. In another example, the beta-carotene in the composition may be about in an amount of about 15 mg.

It is to be appreciated that, when additional scavengers of singlet oxygen such as resveratrol are present in the composition in addition to vitamin A, the total amount of scavengers of singlet oxygen may be greater than the ranges set forth above for the at least one scavenger of singlet oxygen, so long as at least one scavenger of singlet oxygen is present in the amounts set forth above. In addition, other scavengers of singlet oxygen may be used in place of vitamin A, so long as the amount of the at least one scavenger of singlet oxygen is present within the amounts set forth above. When present, the resveratrol is typically included in the composition in an amount of at least 1 mg, more typically in an amount of from 10 mg to 1500 mg, most typically in an amount of from 15 mg to 1000 mg.

Whereas the at least one scavenger of singlet oxygen prevents the initial formation of lipid peroxides, the donor antioxidant reduces peroxyl radicals and inhibits propagation of lipid peroxidation that contributes to hearing loss. More specifically, the donor antioxidant reacts with and reduces peroxyl radicals and thus serves a chain-breaking function to inhibit propagation of lipid peroxidation. As is evident from the chain-breaking function of the donor antioxidant in lipid peroxidation, the donor antioxidant functions within cell membranes. A specific donor antioxidant that is contemplated for use in the composition of the subject invention is vitamin E. Vitamin E is a generic term for all tocols and tocotrienol derivatives with a biological activity of alpha-tocopherol. Primary dietary forms of vitamin E include vitamin E itself and alpha-tocopherol. Trolox®, a water-soluble analogue of alpha-tocopherol commercially available from Hoffman-Laroche, Ltd. of Basel, Switzerland, is a research agent that is typically used as a source of vitamin E.

The donor antioxidant is typically present in the composition, for example, in an amount of at least 75 IU, more typically from 75 IU to 2,000 IU, more typically from 150 to 1,500 IU, most typically from 150 IU to 800 IU. In another example, the donor antioxidant is present in the composition in an amount of at least 75 IU, more typically from 75 IU to 1,500 IU, most typically from 150 IU to 800 IU. As known in the art, a conversion of IU to weight for synthetic vitamin E is 0.66 mg/IU and for natural vitamin E is 0.45 mg/IU. Thus, when the donor antioxidant is synthetic vitamin E, in on example, at least 75 IU of vitamin E is equivalent to at least 50 mg of vitamin E, from 75 to 2,000 IU of synthetic vitamin E is equivalent to from 50 to 1,320 mg of vitamin E, from 150 to 1,500 IU of synthetic vitamin E is equivalent to from 100 to 1,000 mg of vitamin E, and from 150 to 800 IU of synthetic vitamin E is equivalent to from 100 to 536 mg of vitamin E. In another example, when the donor antioxidant is vitamin E, at least 75 IU is equivalent to at least 50 mg of vitamin E, from 75 to 1500 IU of vitamin E is equivalent to from 50 to 1000 mg of vitamin E, and from 150 to 800 IU of vitamin E is equivalent to from 150 to 600 mg of vitamin E. As with the amount and type of vitamin A, specific amounts of the vitamin E present in the composition may be dependent on the body weight of the mammal. In one specific example, the amount of synthetic vitamin E present in the composition is about 3.8 mg/kg body weight. Thus, for an average human weighing about 70 kg, the amount of vitamin E present in the composition may be about 266 mg. In another specific example, the amount of synthetic or natural vitamin E present in the composition is about 2.6 mg/kg body weight. Thus, for an average human weighing about 70 kg, the amount of vitamin E present in the composition may be about 182 mg.

In addition to the at least one scavenger of singlet oxygen and the donor antioxidant, the composition further includes the third antioxidant. While the third antioxidant may be a scavenger of singlet oxygen, the third antioxidant may also be an antioxidant that functions through a different mechanism. When the third antioxidant is a scavenger of singlet oxygen, the at least one scavenger of singlet oxygen is still present in the composition as a separate component from the third antioxidant, and is still present in the composition in the amounts set forth above for the at least one scavenger of singlet oxygen. As a result of the third antioxidant being another scavenger of singlet oxygen, the resulting composition would have at least two scavengers of singlet oxygen.

The third antioxidant is typically vitamin C, which is a scavenger of singlet oxygen and reactive nitrogen species. It is to be appreciated that, although the third antioxidant is typically vitamin C, other antioxidants may be used in place of the vitamin C, and the other antioxidants may function through different mechanisms than vitamin C. The term vitamin C applies to substances that possess antiscorbutic activity and includes two compounds and their salts: L-ascorbic acid (commonly called ascorbic acid) and L-dehydroascorbic acid. In addition to being known as ascorbic acid and L-ascorbic acid, vitamin C is also known as 2,3-didehydro-L-threo-hexano-1,4-lactone, 3-oxo-L-gulofuranolactone, L-threo-hex-2-enonic acid gamma-lactone, L-3-keto-threo-hexuronic acid lactone, L-xylo-ascorbic acid and antiscorbutic vitamin. Vitamin C is known to scavenge both reactive oxygen species and reactive nitrogen species. It can be oxidized by most reactive oxygen and nitrogen species, including superoxide, hydroxyl, peroxyl and nitroxide radicals, as well as such non-radical reactive species as singlet oxygen, peroxynitrite and hypochlorite. Vitamin C thus inhibits lipid peroxidation, oxidative DNA damage, and oxidative protein damage.

In contrast to vitamin A, which functions best under conditions present in most tissues, water-soluble vitamin C is an excellent free radical scavenger in an aqueous phase to thus reduce free radicals at a site different from that of vitamin A. More specifically, ascorbic acid functions to reduce free radicals in fluid, such as in cytoplasmic fluid and/or blood, before the free radicals reach cell membranes.

The third antioxidant is typically present, for example, in an amount of at least 4,000 IU, more typically from 4,000 to 60,000, more typically from 8,000 to 40,000 IU, most typically from 8,000 to 20,000 IU. In another example, the third antioxidant is typically present in an amount of at least 4,000 IU, more typically from 6,000 to 40,000 IU, and most typically from 8,000 to 20,000 IU. Using vitamin C as an example for converting IU to weight units for the third antioxidant, as known in the art, a conversion of IU to weight for vitamin C is 0.05 mg/IU. Thus, at least 4,000 IU of vitamin C is equivalent to at least 200 mg of vitamin C, from 6,000 to 60,000 IU of vitamin C is equivalent to from 300 to 3,000 mg vitamin C, from 6,000 to 40,000 IU of vitamin C is equivalent to from 300 to 2,000 mg, from 8,000 to 40,000 IU of vitamin C is equivalent to from 400 to 2,000 mg vitamin C, and from 8,000 to 20,000 IU vitamin C is equivalent to from 400 to 1,000 mg vitamin C. As with vitamins A and E, specific amounts of the vitamin C or other third antioxidant present in the composition may be dependent on the body weight of the mammal. In one specific example, the amount of vitamin C present in the composition is about 7.14 mg/kg body weight. Thus, for an average human weighing about 70 kg, the amount of vitamin C present in the composition may be about 500 mg.

As set forth above, the composition further includes a vasodilator. Typically, the vasodilator includes magnesium; however, the vasodilator, for purposes of the subject invention, may include other vasodilators in place of or in addition to magnesium, in place of or in addition to those including magnesium, or may include only magnesium or only magnesium-containing compounds. Vasodilators are known in the art for use in preventing hearing loss. Vasodilators including magnesium prevent decreases in cochlear blood flow and oxygenation via biochemical mechanisms involving changes in calcium concentration and prostaglandins. Deficient cochlear blood flow and lack of oxygenation are factors that contribute to hearing loss by causing cell death in sensitive hair cells within a cochlea of the ear. Vasodilators including magnesium have also been found to improve the efficacy of immunosuppressant therapy or carbogen inhalation therapy in recovery from sudden hearing loss. Furthermore, it has been found that magnesium deficiency leads to increased calcium channel permeability and greater influx of calcium into cochlear hair cells, increased glutamate release, and auditory nerve excitotoxicity, each of which play a role in health of the inner ear. Although the vasodilators are known in the art for treating hearing loss, the vasodilators, especially those including magnesium, exhibit an unexpected additive effect when combined with the biologically effective amounts of the at least one scavenger of singlet oxygen, the donor antioxidant, and the third antioxidant, especially when the at least one scavenger of singlet oxygen is vitamin A, the donor antioxidant is vitamin E, and the third antioxidant is vitamin C for purposes of treating noise-induced hearing loss. Similar excellent effectiveness has also been found when the composition is used to treat side effects of antibiotic treatment including antibiotic-induced hearing loss. The additive effect referred to above is greater than not only the most efficacious of the components for treating hearing loss, but typically greater than the sum of the effects of each of the components for treating hearing loss. While vasodilators other than those including magnesium are envisioned for purposes of the present invention, additive effects are not observed with all vasodilators. For example, betahistine, which is another known vasodilator, does not exhibit an additive effect as is evident from FIG. 1. Specific effects of the composition of the subject invention on treating noise-induced hearing loss and side effects of antibiotic treatment are described in further detail below.

The vasodilator including magnesium typically includes a magnesium salt or magnesium salt complex and, more specifically, magnesium sulfate or magnesium citrate. Other vasodilators including magnesium that may be suitable for purposes of the subject invention include; magnesium acetate, magnesium aspartate, magnesium carbonate, magnesium chloride, magnesium fumarate, magnesium gluconate, magnesium glycinate, magnesium hydroxide, magnesium lactate, magnesium oxide, magnesium salicylate, magnesium stearate, and magnesium sulfate. Other representative salts include but are not limited to; hydrobromide, hydrochloride, bisulfate, nitrate, arginate, ascorbate, oxalate, valerate, oleate, palmitate, laurate, borate, benzoate, phosphate, tosylate, maleate, fumarate, succinate, taurate, tartrate, naphthylate, mesylate, glucoheptonate, lactobionate and laurylsulphonate salts.

Typically, the vasodilator is present in the composition in an amount of at least 50 mg. For example, when the vasodilator is magnesium, the magnesium is typically present in an amount of from 50 to 450 mg, most typically from 100 to 350 mg. As with vitamins A, C, and E, specific amounts of the vasodilator present in the composition may be dependent on the body weight of the mammal. In one specific example, the amount of the vasodilator including magnesium present in the composition is about 4.46 mg/kg body weight. Thus, for an average human weighing about 70 kg, the amount of the vasodilator including magnesium present in the composition may be about 312 mg. In another example, the amount of the vasodilator including magnesium present in the composition is about 2.14 mg/kg body weight. Thus, for an average human weighing about 70 kg, the amount of the vasodilator including magnesium present in the composition may be about 150 mg.

Non-limiting examples of amounts of the typical components included in the composition, along with more and most typical amounts, are summarized in Table 1 below.

TABLE 1

| Component | | Amount | More Typical Amount | Most Typical Amount | Typical Dosage, mg/kg body weight |
|---|---|---|---|---|---|
| Vitamin A | | ≥830 IU | 830-10,000 IU | 2100-8,000 IU | 0.0178 mg/kg |
| | Vitamin A As beta-carotene | ≥830 IU | 830-50,000 IU | 2,000-30,000 IU | 0.257 mg/kg |
| Vitamin C | | ≥4,000 IU | 4,000-60,000 IU | 8,000-20,000 IU | 7.14 mg/kg |
| Vitamin E | | ≥75 IU | 75-2000 IU | 150-800 IU | 3.8 mg/kg (synthetic) |
| Magnesium | | ≥50 mg | 50-450 mg | 100-350 mg | 4.46 mg/kg |

With respect to Table 1, the amounts specified for the antioxidants and the vasodilator correlate, in terms of biological effectiveness, to amounts used for humans. Furthermore, it is to be appreciated that the biologically effective amounts of the antioxidants and vasodilator may be lower within the above ranges for children than for the average human, based on lower US recommended daily allowances and maximum intake levels for children. This is evident based on the typical dosages in Table 1 based on mg/kg.

Other non-limiting examples of amounts of the typical components included in the composition, along with more and most typical amounts, are summarized in Table 2 below.

TABLE 2

| Component | | Amount | More Typical Amount | Most Typical Amount | Typical Dosage, mg/kg body weight |
|---|---|---|---|---|---|
| Vitamin A | | ≥830 IU | 830-120,000 IU | 2,100-70,000 IU | — |
| | Vitamin A As Retinol | ≥830 IU | 830-50,000 IU | 2,100-5,900 IU | 0.0178 mg/kg |
| | Vitamin A As beta-carotene | ≥10,000 IU | 10,000-120,000 IU | 25,000-70,000 IU | 0.214 mg/kg |
| Vitamin C | | ≥4,000 IU | 6,000-40,000 IU | 8,000-20,000 IU | 7.14 mg/kg |
| Vitamin E | | ≥75 IU | 75-1,500 IU | 150-800 IU | 2.6 mg/kg |
| Magnesium | | ≥50 mg | 50-450 mg | 100-350 mg | 2.14 mg/kg |

With respect to Table 2, the amounts specified for the antioxidants and the vasodilator correlate, in terms of biological effectiveness, to amounts used in animal studies on guinea pigs. Furthermore, it is to be appreciated that the biologically effective amounts of the antioxidants and vasodilator may be lower within the above ranges for children than for the average human, based on lower U.S. recommended daily allowances and maximum intake levels for children. This is evident based on the typical dosages in Table 2 based on mg/kg.

In addition to the antioxidants and vasodilator, other components may also be present in the composition for treating hearing loss, as well as for treating the side effects of the antibiotic treatment. For example, in one embodiment, the composition further includes a withanolide. Withanolide have been suggested for use in anti-inflammatory, anti-tumor, cytotoxic, and immunological applications. One example of a specific withanolide that may be included in the composition of the subject invention is the withanolide extracted from day lily plants. The extract is a powerful natural antioxidant which may be effective in preventing cell death in the inner ear by interrupting the cell-death pathway initiated by differentiation of the auditory nerve. When included in the composition, the withanolide may be present in an amount of at least 10 ppm, more typically from 10 to 1000 ppm. Additional components, besides withanolides, can also be included. Typically, the composition is free of components that interfere with the biological mechanisms through which the at least one scavenger of singlet oxygen, the donor antioxidant, the third antioxidant, and the vasodilator function. The composition is also typically free of additional components that could degrade or neutralize the at least one scavenger of singlet oxygen, the donor antioxidant, the third antioxidant, and the vasodilator function when mixed therewith prior to internally administering the composition to the mammal. Those of skill in the art can readily identify such components in view of the mechanisms by which the individual components in the composition function as set forth above (e.g., components that cause vasoconstriction, various oxidizing agents, etc.).

It is also to be appreciated that, even if additional components are present in the composition that could interfere with the mechanisms by which the at least one scavenger of singlet oxygen, the donor antioxidant, the third antioxidant, and the vasodilator function, the composition described above is still effective for purposes of treating side effects of the antibiotic treatment. As one example, and as described in further detail below, the composition including the at least one scavenger of singlet oxygen, the donor antioxidant, the third antioxidant, and the vasodilator is still effective for treating hearing loss and other side effects of antibiotic treatment when administered in conjunction with aminoglycoside antibiotics (as made clear with reference to FIG. 5). This is true even though aminoglycoside antibiotics, themselves, are responsible for causing hearing loss and other side effects such as kidney damage and loss of balance through free radical formation.

In view of the fact that components as detrimental as aminoglycosides can be administered in conjunction with the composition described above, it is clear that additional components that are less detrimental to the specific mechanisms by which the at least one scavenger of singlet oxygen, the donor antioxidant, the third antioxidant, and the vasodilator function can also be present in the composition with an expectation that the composition maintains effectiveness for purposes of treating side effects of antibiotic treatment such as antibiotic-induced hearing loss. Examples of some additional components that may be included in the composition include, but are not limited to, excipients, flavoring agents, fillers, binders, and additional vitamins or minerals not specifically mentioned herein.

As alluded to above, the method of treating hearing loss and the method of treating side effects from antibiotic treatment of the instant invention includes the step of internally administering the composition of the subject invention to a mammal. More specifically, the instant method is for treating side effects of antibiotic treatment such as antibiotic-induced hearing loss, kidney damage, and loss of balance. The examples of the composition may be orally administered to the mammal, such as in the form of a tablet, liquid, gel, etc. Alternatively, the composition may be intravenously administered to the mammal through an IV or an injection of the composition. When specifically used to treat antibiotic-induced hearing loss, the composition may also be locally administered via the round window membrane of the cochlea. As a specific example, the vitamins A, C, and E, the vasodilator including magnesium, and the optional components may be first combined to form the composition, with the composition then administered to the mammal. Alternatively, the vitamins A, C, and E, the vasodilator including magnesium, and the other optional components may be separately administered, in which case the composition forms within the mammal.

For purposes of the subject invention, hearing loss may be objectively measured in terms of differences in threshold shift, or through measurement of a percentage of hair cell loss. In guinea pig studies, hearing loss and the efficacy of the composition for treating antibiotic-induced hearing loss may be measured as an average difference in threshold shift from baseline threshold sensitivity at 4, 8, and 16 kHz, as compared to an untreated control, after exposure to 120 decibel SPL Octave Band Noise centered at 4 kHz for five hours. Larger differences in threshold shift correlate to less hearing loss and greater efficacy of the composition for treating the antibiotic-induced hearing loss.

It is has been shown that hair cell loss correlates to threshold shift. For example, in guinea pig ears that recover from temporary threshold shift, morphological damage is limited to tips of stereocilia in a third row of outer hair cells (OHCs) whereas ears from animals with permanent threshold shift have damage to all three rows of OHCs and, in some cases, the inner hair cells (IHCs), with damage throughout the length of the stereocilia as well as the to the body of the hair cell.

In one embodiment, the composition of the present invention is administered to the mammal within three days of trauma to the inner ear of the mammal in order to alleviate permanent threshold shift. It is to be appreciated that by administering the composition within three days of trauma, treatment prior to trauma is also contemplated through the method of the present invention. Data from animal studies indicate that temporary threshold shift measured 24 hours post-trauma is well-correlated with permanent threshold shift. Given the relationship between temporary threshold shift and permanent threshold shift, it is clinically beneficial to reduce temporary threshold shift. As such, the composition is typically administered within one day of trauma to the inner ear of the mammal. Even so, it is expected that treatment within three days with the composition of the present invention is substantially as effective in minimizing permanent threshold shift as treatment within one day.

Treatment within three days is most appropriate when the mammal has sustained trauma to the inner ear through unexpected loud noise or other trauma. Ideally, the composition is administered to the mammal prior to trauma to the inner ear. Treatment prior to trauma is most feasible when the mammal is preparing for sustaining trauma to the inner ear. For example, the composition may be administered prior to restoration surgery performed on the inner ear. As another example, if a person will be firing a weapon or attending an event such as a rock concert, the person may begin treatment prior to sustaining the trauma to the inner ear to attain the best results.

After initial administration of the composition, the composition is typically administered to the mammal each day for at least five days following the trauma to the inner ear of the mammal. Although excellent results have been achieved through such treatment, it is to be appreciated that other treatment regimens may also prove efficacious for purposes of the present invention.

For the method of treating side effects of antibiotic treatment, the composition is internally administered to the mammal in conjunction with administration of the antibiotic. In this regard, the method also includes the step of internally administering the antibiotic, which antibiotic is capable of inducing hearing loss in the mammal. It is to be appreciated that, even though the antibiotic with which the composition is administered is capable of inducing hearing loss, the method of the instant invention is not strictly limited to treatment of hearing loss that is induced by the antibiotics. More specifically, the method of the instant invention proscribes the step of administering the subject composition in conjunction with administration of the antibiotic for any purpose including for treating any side effect of the antibiotics including not only antibiotic-induced hearing loss, but also kidney damage, loss of balance, among other side effects.

Specific non-limiting examples of antibiotics that are capable of inducing hearing loss in mammals include aminoglycoside antibiotics such as amikacin, arbekacin, gentamicin, kanamycin, neomycin, netilmicin, paromomycin, rhodostreptomycin, streptomycin, tobramycin, and apramycin; and glycopeptide antibiotics such as vancomycin, teicoplanin, telavancin, bleomycin, ramoplanin, and decaplanin. The treatment is particularly effective against aminoglycoside-induced side effects. In one specific embodiment, the antibiotic is gentamicin, which is commonly used in developing countries due to low cost and effectiveness against certain drug-resistant diseases.

The dosages of the antibiotic that are administered to the mammal may vary within the medically-accepted ranges for therapeutic treatment, as may the number of days over which the antibiotic is administered. The antibiotic is typically administered daily. For purposes of objectively establishing the effectiveness of the treatment described herein, a dosage of 140 g of gentamicin was administered to guinea pigs for a period of 16 days. However, it is to be appreciated that the specific dosages and days over which the antibiotic is administered are not material for purposes of establishing the viability of the treatment described herein so long as the composition described herein is administered in conjunction with administration of the antibiotic (although the effectiveness of the treatment described herein may vary based upon dosages and days over which the antibiotics are administered).

For purposes of the instant disclosure, administration of the composition described herein "in conjunction with" administration of the antibiotic refers to a connection in the administration of the composition and the antibiotic during the course of antibiotic treatment. To maximize effectiveness of the treatment described herein, it is desirable to establish stable serum levels of the at least one scavenger of singlet oxygen, the donor antioxidant, the third antioxidant, and the vasodilator at the time that the antibiotics reach serum levels within the mammal that cause material side effects such as hearing loss. Typically, the composition is internally administered to the mammal no longer than three days after administration of a first dosage of the antibiotic, which is sufficient to achieve the stable serum levels of the at least one scavenger of singlet oxygen, the donor antioxidant, the third antioxidant, and the vasodilator before the antibiotics begin to materially cause the side effects such as hearing loss. In one embodiment, the composition is internally administered prior to administration of the first dosage of the antibiotic. In this embodiment, the composition may be administered at least five days, alternatively at least ten days, prior to administration of the first dosage of the antibiotic for purposes of maximizing the effectiveness of the treatment for side effects of antibiotic treatment described herein.

Once administration of the composition has begun, the composition is typically administered each day the antibiotic is administered to maintain adequate serum levels of the at least one scavenger of singlet oxygen, the donor antioxidant, the third antioxidant, and the vasodilator. Additionally, the composition is typically administered for at least 1, 2, 3, 4, 5, 6, 7, 8, 9, 10, 11, 12, 13, 14, 15, 16, 17, 18, 19, 20, or 21 days following cessation of administration of the antibiotic. This is typically performed for purposes of ensuring that adequate serum levels of the at least one scavenger of singlet oxygen, the donor antioxidant, the third antioxidant, and the vasodilator are maintained until the serum levels of the antibiotic decrease, and typically until all of the additional free radicals formed secondary to the antibiotic treatment are eliminated.

As described in further detail in the Examples section below, an average difference in threshold shift in mammals from baseline threshold sensitivity at 4, 8, and 16 kHz, as compared to an untreated control, is at least 25 decibels after exposure to 120 decibel SPL Octave Band Noise centered at 4 kHz for five hours. More specifically, the threshold shift in mammals treated with the composition of the present invention is expected to be at least 25 decibels lower than the threshold shift in mammals that are treated with a control saline solution. To obtain those results, the composition is orally administered one hour prior to exposure to the noise and administered again each day for five days subsequent to the exposure to the noise. The threshold shift is measured 10 days after exposure to the noise using auditory brainstem response (ABR) testing. Similar results would be anticipated using other alternative measures of auditory or sensory cell function, such as psychophysical tests or optoacoustic emission measures. While effectiveness of treatment in accordance with the method of the instant invention is objectively proven herein through measurement of shifts in threshold hearing loss, it is to be appreciated that the method is not strictly limited to treatment of hearing loss alone and broadly encompasses administration of the subject composition in conjunction with administration of the particular antibiotics described herein.

Figure 5:
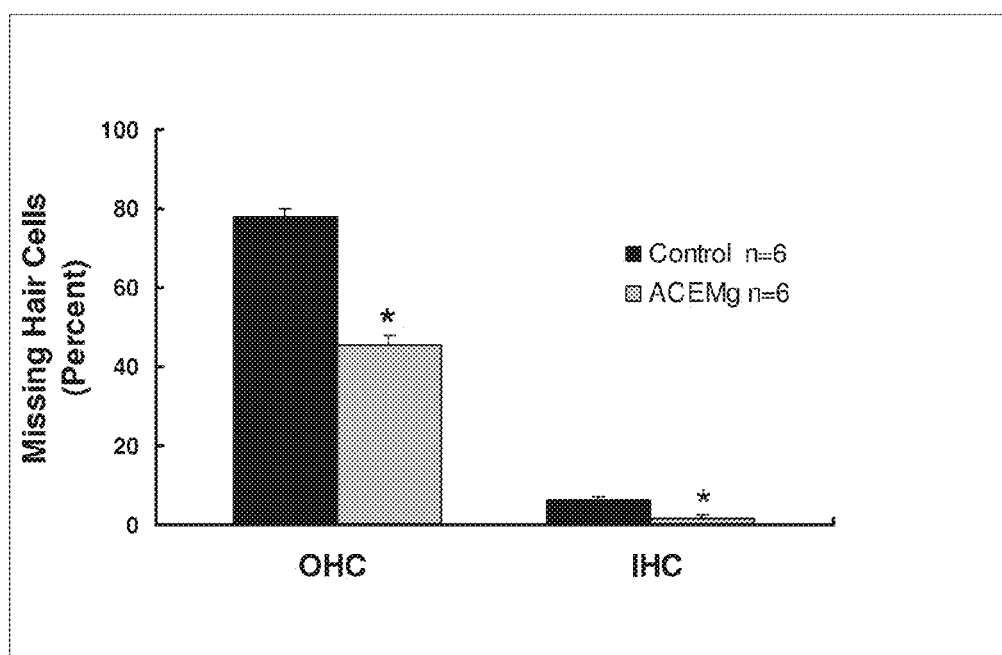
FIG. 5 is a graph showing the effect of treatment of side effects of antibiotic treatment, as a measurement of percentage of outer hair cells and inner hair cells lost in guinea pigs, when the composition including vitamins A, C, and E and magnesium is administered in conjunction with administration of aminoglycoside antibiotics in accordance with the method of the subject invention versus a control in which aminoglycoside antibiotic is administered alone.

In addition, outer hair cell loss and inner hair cell loss is measured both in the whole cochlea and in a trauma region of the cochlea. After treatment according to the method of the present invention, outer hair cell loss in the whole cochlea is less than 10%, and inner hair cell loss in the whole cochlea is less than 5%. Outer cell hair loss in the trauma region is less than 20%, while inner hair cell loss in the trauma region is less than 10%. For the method of treatment in accordance with the present invention, as shown in FIG. 5, outer hair cell loss in the whole cochlea is less than 50%, while inner hair cell loss in the whole cochlea is less than 5%. To obtain those results, the composition is orally administered to guinea pigs for 10 to 16 days prior to first administration of the antibiotic, and the composition and antibiotic are administered again each day for forty days. The guinea pigs are then euthanized and the hair cells counted. Conversely, when the antibiotic is administered for forty days without administering the composition described herein in conjunction with the antibiotic, outer hair cell loss approaches 80%, while inner hair cell loss is about 8%.

The following examples, as presented herein, are intended to illustrate and not limit the invention.

REFERENCE EXAMPLE

A method of treating noise-induced hearing loss is performed on guinea pigs (NIH outbred strain, 250-350 grams) as a reference example for the instant application. The guinea pigs are used due to their extensive use in auditory research, including studies on noise-induced hearing loss, and because they provide a model similar to humans in terms of development. Six guinea pigs are subject to treatment with the composition of the present invention. In order to determine efficacy of the composition of the present invention in treating hearing loss, baseline threshold sensitivity of the guinea pigs is measured binaurally using auditory brainstem response testing at 4, 8, and 16 kHz. The guinea pigs are then treated with vitamins A, C, E, and magnesium (referred to in FIGS. 2-7 as "ACEMg") in the amounts shown in Table 3. The amounts shown in Table 3 are approximately 3 times expected human doses based on more rapid metabolism of guinea pigs relative to humans.

TABLE 3

| Component | Parts by Weight |
| --- | --- |
| Vitamin A (beta-carotene) | 2.1 mg/kg p.o. |
| Vitamin C (Ascorbic acid) | 71.4 mg/kg s.c |
| Vitamin E (Trolox ®) | 26 mg/kg s.c. |
| Magnesium (MgSO4) | 2.85 mmol/kg s.c. |

One hour later, the guinea pigs are exposed to 120-dB SPL Octave Band Noise centered at 4 kHz for 5 hours to cause trauma to inner ears of the guinea pigs. The noise is sufficient to cause permanent threshold shift, i.e., permanent hearing loss. The composition of the present invention is administered immediately post-exposure to the noise, and again each day for 5 days after the trauma. Ten days after the trauma, auditory sensitivity is measured using ABR. For ABR testing, the guinea pigs are anesthetized with 40 mg/kg ketamine and 10 mg/kg xylazine and placed on a warm heating pad in a sound attenuated chamber. ABR thresholds are determined at 4, 8 and 16 kHz frequencies. To test for the ABR thresholds, tone bursts 10 ms in duration (0.5 ms rise/fall) are presented at a rate of 17/sec. Up to 1024 responses are collected and averaged for each signal frequency to provide a measure of threshold shift at each frequency. Estimates of permanent hearing loss, shown in FIG. 2 in terms of threshold shift in decibels, are calculated as average threshold shift across ears and across frequencies.

Figure 3:
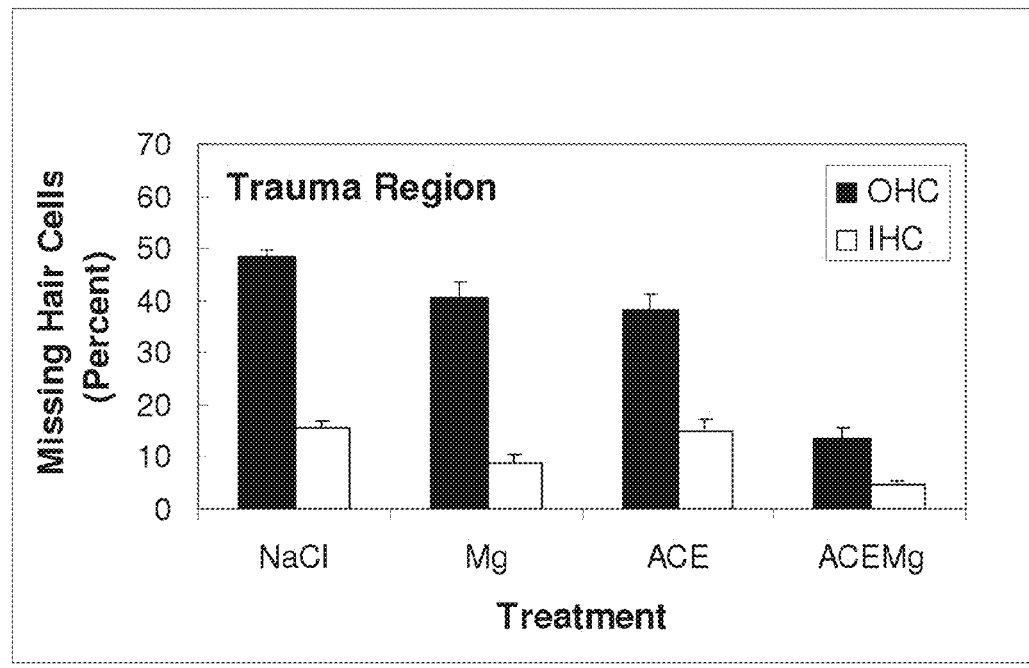
FIG. 3 is a graph showing the effect of treatment in accordance with the instant invention using the composition of the subject invention and treatments using Comparative Examples of compositions of FIG. 2 on an amount of missing hair cells in the region of the cochlea that is most damaged after the noise exposure specified above for FIG. 2.
Figure 4:
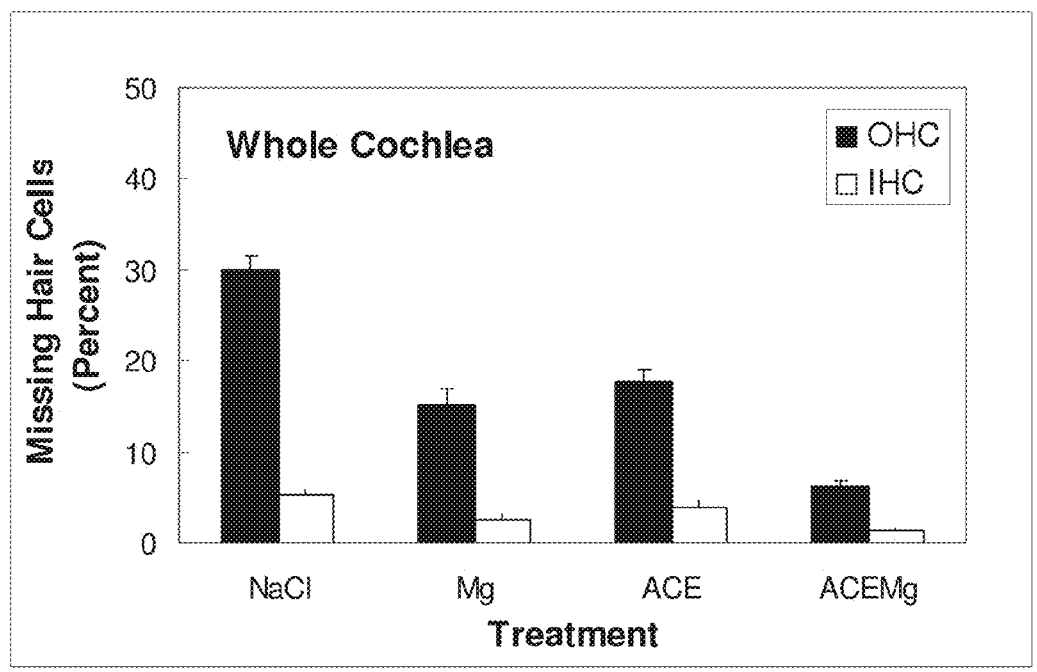
FIG. 4 is a graph showing the effect of treatment in accordance with the instant invention using the composition including vitamins A, C, and E and magnesium and treatments using Comparative Examples of compositions of FIG. 2 on an amount of missing hair cells in the whole cochlea after the noise exposure specified above for FIG. 2.

After ABR testing, the guinea pigs are deeply anesthetized and decapitated. Temporal bones are quickly removed, dissected open and fixed with 4% paraformaldehyde. The following day, an otic capsule, lateral wall, and tectorial membrane are removed, and a bony modiolus is carefully detached. Organ of Corti tissue, attached to the modiolus, is permeabilized with 0.3% Triton-X and incubated with rhodamine phalloidin diluted 1:100 in phosphate buffered saline (30 min). After washing the tissues, individual turns from the organ of Corti are dissected, mounted on microscope slides, and examined and photographed using a Leica DMRB epiflourescence microscope. Hair cell counts are conducted, and cytocochleograms are prepared as known in the art. Referring to FIGS. 3 and 4, percentages of missing inner hair cells (IHC) and outer hair cells (OHC) are determined based on the hair cell counts.

Example 1

The method of treating side effects of antibiotic treatment with the composition of the present invention is again performed on guinea pigs (normal hearing, male, pigmented). Six guinea pigs are subject to antibiotic administration and treatment with the composition of the present invention. The guinea pigs were fed with a chow containing the composition including beta-carotene, vitamin C, vitamin E, and magnesium in the amounts shown in Table 3 for 10 days prior to administration of a first dosage of gentamicin antibiotic, and were fed the same chow every day for 41 days. The guinea pigs consumed a normal diet sufficient to allow them to gain weight. Gentamicin was administered to the guinea pigs subcutaneously once a day for 16 consecutive days after administration of the first dosage of the gentamicin. Body weights were monitored and the guinea pigs were observed for clinical signs of systemic toxicity. Guinea pigs losing weight were treated with subcutaneous saline and the chow was administered orally as gruel. Fourteen days following cessation of antibiotic treatment, the guinea pigs were euthanized, left cochleae harvested, and quantitative sensory hair cell assessments were performed. The amounts shown in Table 4 are approximately 10 times expected human doses based on more rapid metabolism of guinea pigs relative to humans.

TABLE 4

| Component | Parts by Weight |
| --- | --- |
| Antibiotic (Gentamicin) | 140 mg/kg |
| Vitamin A (beta-carotene) | 1 g/kg p.o. |
| Vitamin C (Ascorbic acid) | 20 g/kg s.c |
| Vitamin E (Trolox ®) | 7 g/kg s.c. |
| Magnesium (MgSO4) | 30 g/kg s.c. |

Comparative Example 1

Figure 2:
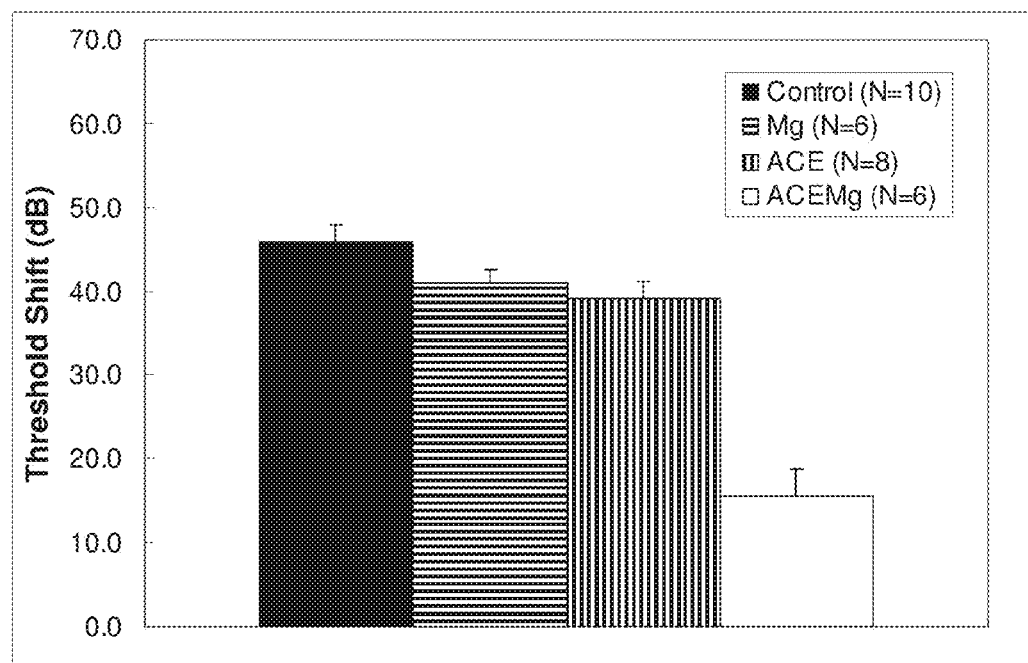
FIG. 2 is a graph showing the effect of treatment in accordance with the instant invention using a composition including vitamins A, C, and E and magnesium, and comparative examples of treatments using compositions that include only some of those components, on average reduction of a threshold shift in guinea pigs from baseline threshold sensitivity at 4, 8, and 16 kHz after exposure to 120 decibel SPL Octave Band Noise centered at 4 kHz for five hours.

Guinea pigs are treated with other compositions in order to compare the efficacy of the composition of the present invention with the other compositions. For example, guinea pigs are separately treated in the same way as specified above in the Example with the following compositions: a saline (NaCl) composition as a control, a composition including only magnesium sulfate (2.85 mmol/kg), or a composition including only vitamins A (2.1 mg/kg beta-carotene), C (71.4 mg/kg ascorbic acid), and E (26 mg/kg Trolox®) ("ACE"). The guinea pigs are subjected to the same ABR testing, and the components of the ear are dissected, as described above in the Example to provide information on threshold shift and hair cell loss. Threshold shift and hair cell loss resulting from treatment with the other compositions are shown in FIGS. 2-4.

Comparative Example 2

Guinea pigs are treated with a composition of vitamin E alone, betahistine alone, or a combination of betahistine and vitamin E to determine if results similar to those achieved with the composition of the present invention including magnesium can be achieved by substituting betahistine for the magnesium. The results of treatment with vitamin E, betahistine, or combination of vitamin E and betahistine are shown in FIG. 1. In one comparative example, guinea pigs are treated once daily with 100 mg/kg vitamin E (Trolox®), 30 mg/kg Betahistine, or a combination of 100 mg/kg Trolox® and 30 mg/kg Betahistine. Five guinea pigs are treated with each of the different compositions. In another comparative example, four guinea pigs are separately treated with 50 mg/kg Trolox® twice daily, 18 mg/kg Betahistine (one dose immediately pre-noise exposure), or a combination of 50 mg/kg vitamin E (Trolox®) and 18 mg/kg Betahistine (N=4 animals per group). Control data are from 18 animals treated with saline delivered either IP (N=11) or IV (N=7). The guinea pigs are subjected to ABR testing, and the components of the ear are dissected, both as described above in the Example, to provide information on threshold shift and hair cell loss.

Comparative Example 3

Six guinea pigs are subject to antibiotic administration in the absence of treatment with the composition of the present invention. Gentamicin was administered to the guinea pigs subcutaneously in an amount of 140 mg/kg body weight once a day for 16 consecutive days after administration of the first dosage of the gentamicin. Body weights were monitored and the guinea pigs were observed for clinical signs of systemic toxicity. Guinea pigs losing weight were treated with subcutaneous saline. The weight gain of the six guinea pigs, which were on a non-supplemented diet, was statistically the same as the guinea pigs in Example 1. Fourteen days following cessation of antibiotic treatment, the guinea pigs were euthanized, left cochleae harvested, and quantitative sensory hair cell assessments were performed.

Comparative Example 4

Figure 6:
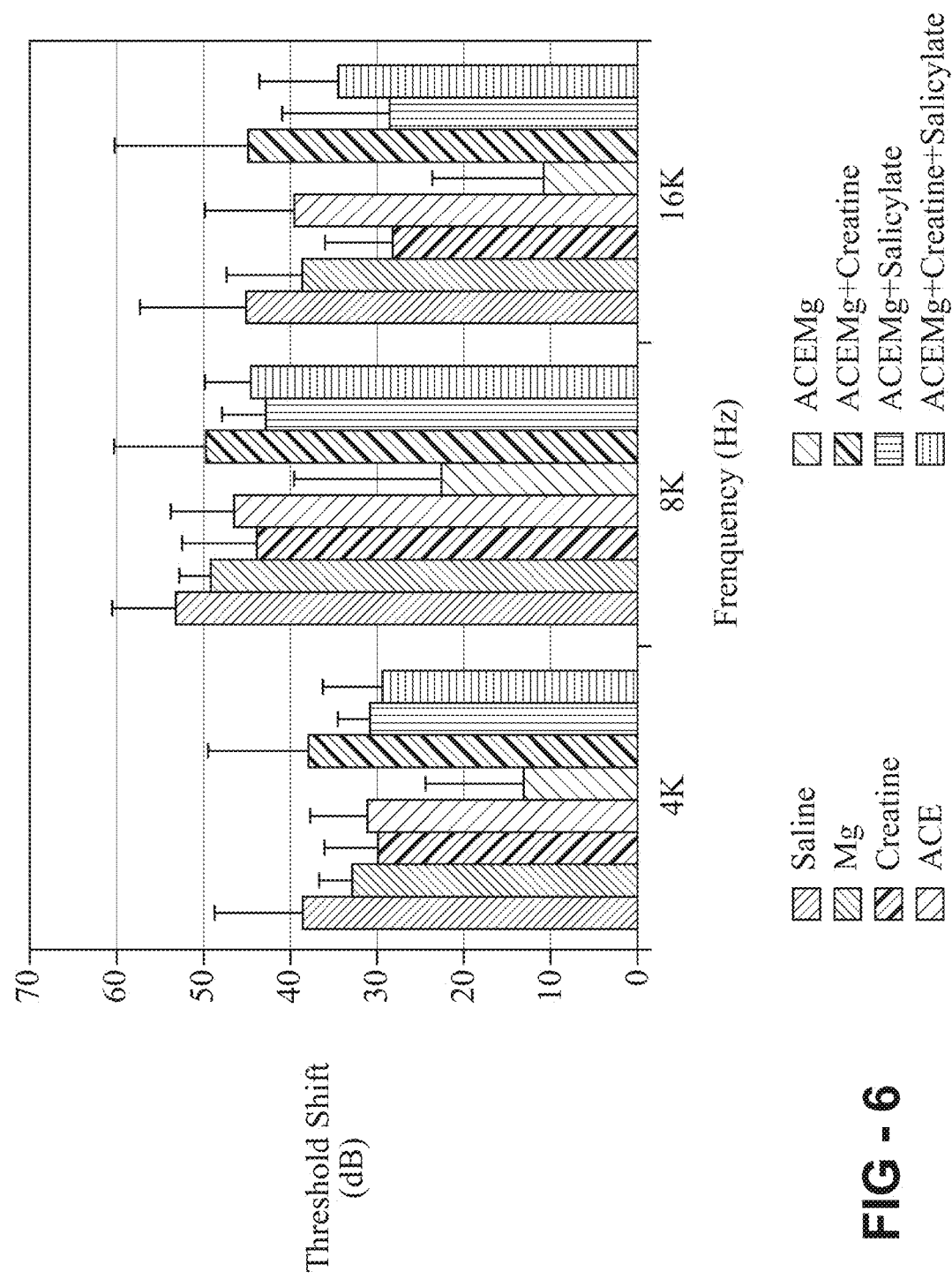
FIG. 6 is a graph showing a mean threshold shift of hearing loss in guinea pigs treated with an inventive composition consisting essentially of vitamin A, vitamin C, vitamin E, and magnesium, and treated with comparative compositions including i) saline, ii) magnesium, iii) vitamins A, C, and E, iv) creatine, v) vitamin A, vitamin C, vitamin E, magnesium, and creatine, and vi) vitamin A, vitamin C, vitamin E, magnesium, creatine, and salicylate, where the mean threshold shift is measured at baseline threshold sensitivities of 4, 8, and 16 kHz after exposure to 120 decibel SPL Octave Band Noise centered at 4 kHz for five hours.
Figure 7:
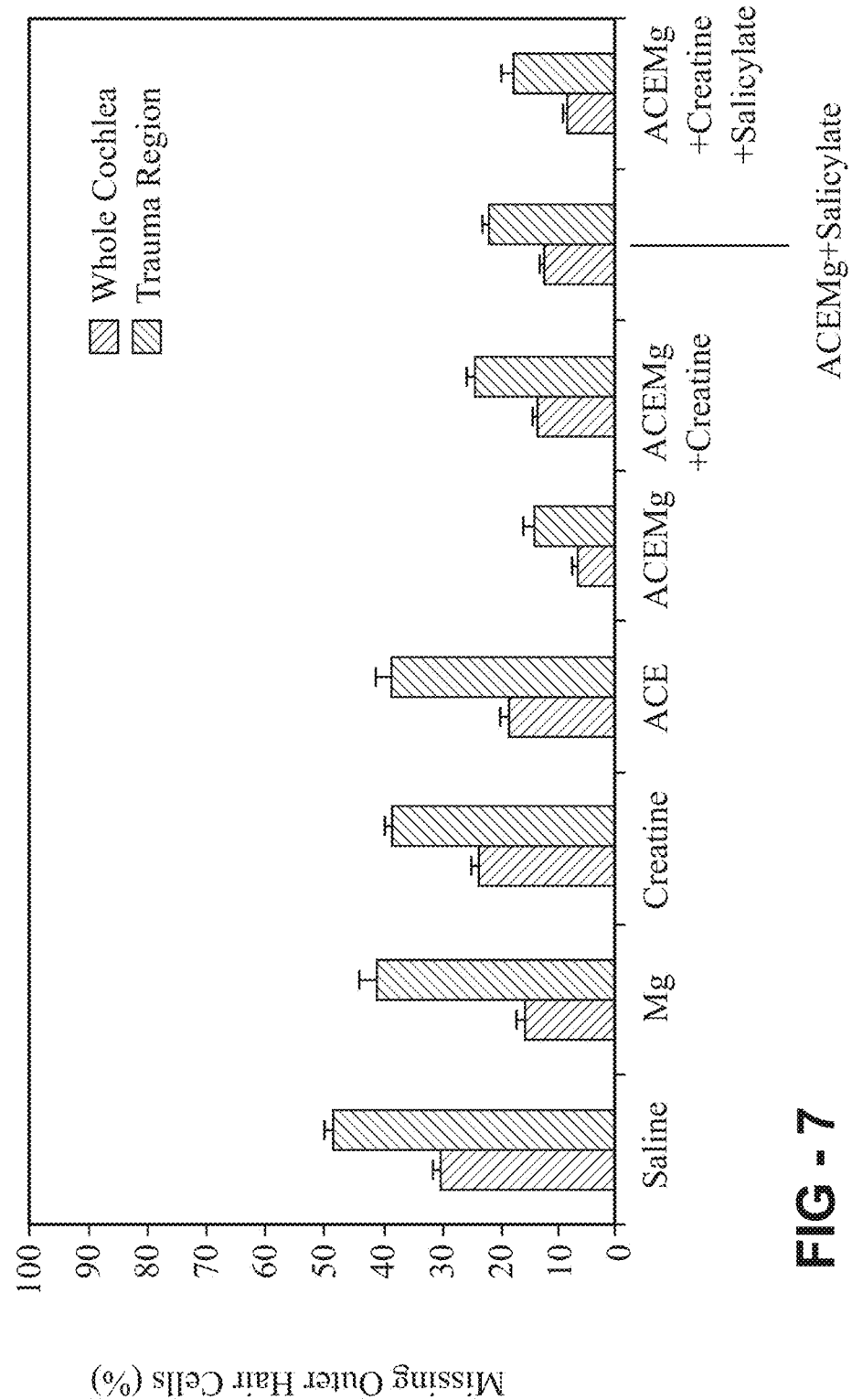
FIG. 7 is a graph showing side effects of treatment of the guinea pigs by an inventive composition consisting essentially of vitamin A, vitamin C, vitamin E, and magnesium, and by comparative compositions including i) saline, ii) magnesium, iii) vitamins A, C, and E, iv) creatine, v) vitamin A, vitamin C, vitamin E, magnesium, and creatine, and vi) vitamin A, vitamin C, vitamin E, magnesium, creatine, and salicylate, the side effects of the treatment being a measurement of percentage of outer hair cells lost in the guinea pig in the whole cochlea and in the trauma region after the noise exposure.

Eight groups of guinea pigs (where the number of guinea pigs ranges from 5 guinea pigs to 10 guinea pigs per group) are respectively treated with other compositions to compare the efficacy of the "ACEMg" composition of the present invention with the other compositions. For example, the guinea pigs are separately treated in the same way as specified above in the Example with the following compositions: a saline (NaCl) composition as a control, a composition including only $MgSO_4$ (2.85 mmol/kg), a composition including creatine (3% monohydrate diet), a composition including only vitamins A (2.1 mg/kg beta-carotene), C (71.4 mg/kg ascorbic acid), and E (26 mg/kg Trolox®) ("ACE"), a composition including "ACEMg" (2.1 mg/kg of vitamin A, 71.4 mg/kg of vitamin C, 26 mg/kg of vitamin E, and 2.85 mmol/kg of $MgSO_4$) and creatine (3% monohydrate diet), and a composition including "ACEMg" (2.1 mg/kg of vitamin A, 71.4 mg/kg of vitamin C, 26 mg/kg of vitamin E, and 2.85 mmol/kg of $MgSO_4$), creatine (3% monohydrate diet), and salicylate (75 mg/kg). The eight groups of guinea pigs are exposed to the same ABR testing, and the components of the ear are dissected as previously described in the Example to provide information on threshold shift and outer hair cell loss. The threshold shift of hearing loss and the outer hair cell loss resulting from treatment with the "ACEMg" composition and the other compositions tested are shown in FIGS. 6 and 7, respectively.

Results

Referring to FIGS. 2-4, the effect in treating hearing loss with composition of the present invention including vitamins A, C, E, and magnesium is clearly greater than that associated with the effectiveness of a composition including only magnesium or only vitamins A, C, and E. More specifically, treatment with the composition of the present invention results in a threshold shift of less than 20 decibels, as averaged across all frequencies, while treatment with a control saline solution results in a threshold shift of about 45. As such, a difference in threshold shift between treatment with the composition of the present invention and treatment with the control of saline solution is over 25 decibels. Furthermore, the difference in threshold shift between the composition of the present invention and the control saline solution is greater than the sum of differences in threshold shifts for magnesium or vitamins A, C, and E alone and the control saline solution. Specifically, the sum of the differences in threshold shifts for magnesium and vitamins A, C, and E alone is about 12 decibels. It is to be understood that the decibel scale is a logarithmic scale. As such, a difference in the threshold shift of hearing loss of 12 decibels for the composition consisting essentially of magnesium and vitamins A, C, and E and Mg represents a fourfold difference in efficacy compared to the other compositions tested. This result demonstrates a highly synergistic interaction among the individual components of the composition consisting essentially of magnesium and vitamins A, C, and E. Furthermore, the difference in the threshold shift of hearing loss of about 45 decibels for the composition including saline and the difference in the threshold shift of hearing loss of about 20 decibels for the composition including vitamins A, C, and E is similar to the difference between a moderate handicap and a severe handicap.

Consistent with the reduction in noise-induced hearing loss, hair cell counts revealed significantly reduced sensory cell death with Mg or A, C, and E, with the greatest protection observed after treatment with vitamins A, C, E, and magnesium. More specifically, less than 10% of outer hair cells and less than 5% of inner hair cells in the whole cochlea are missing after treatment with the composition of the present invention including Mg and vitamins A, C, and E. In the trauma region, less than 20% of outer hair cells and less than 10% of inner hair cells in the whole cochlea are missing after treatment with the composition of the present invention including Mg and vitamins A, C, and E. As shown by FIGS. 3 and 4, the reduction in percentage of missing hair cells after treatment with the composition of the present invention is more than the sum of the reductions in missing hair cells observed when magnesium or vitamins A, C, and E are used alone as compared to the percentage of hair cell loss when saline is used.

Furthermore, as shown in FIG. 1, the Comparative Examples in which vitamin E, betahistine, or a combination of vitamin E and betahistine are used clearly do not exhibit the same additive effect that is observed when magnesium is used as the vasodilator in combination with the vitamins to treat noise-induced hearing loss. More specifically, saline treated control animals (white bars) show the greatest hearing loss 10 days post noise. Animals treated with Vitamin E (Trolox®: 100 mg/kg once daily or 50 mg/kg twice daily, diagonal lined bars) have less permanent hearing loss than control animals. Animals treated with the vasodilator betahistine (30 mg/kg, once daily, vertical striped bars; or one 18 mg/kg dose pre-noise, horizontal striped bars) show approximately the same amount of protection as those treated with vitamin E. Animals treated with a combination of vitamin E and betahistine (50 mg/kg Trolox® twice daily+18 mg/kg betahistine twice daily, or 100 mg/kg Trolox® once/daily+30 mg/kg betahistine once/daily; see dark bars with white diagonal hatch) do not have any additive protection against noise-induced hearing loss beyond that of either single agent alone. As such, not all vasodilators are as effective as magnesium in combination with the vitamins.

In terms of comparison of the method of treating side effects of antibiotic treatment in terms of measurement of antibiotic-induced hearing loss as shown in Example 1 with Comparative Example 3, dramatic cell death of outer hair cells was observed through the treatment of Comparative Example 3 due to the ototoxic effects of the gentamicin antibiotic. Referring to FIG. 5, it can be seen that statistically significant reduction in antibiotic-induced hearing loss (as gauged by quantitative sensory hair cell assessments) through the treatment described in Example 1 versus the treatment described in Comparative Example 3. In particular, both outer and inner hair cells are protected through the treatment in accordance with Example 1.

Referring now to FIGS. 6 and 7, the effect in treating hearing loss with the composition of the present invention which consists essentially of vitamin A, vitamin C, vitamin E, and a vasodilator comprising magnesium ("ACEMg") is clearly superior to the effect of treating hearing loss with the other compositions tested. As shown in FIG. 6, treatment with the composition consisting essentially of "ACEMg" results in a threshold shift of hearing loss of less than 20 decibels, as averaged across all frequencies. Treatment with a control saline solution results in a threshold shift of 45 decibels, as averaged across all frequencies. Treatment with the composition including magnesium results in a threshold shift of about 41 decibels, as averaged across all frequencies, while treatment with the composition including "ACE" results in a threshold shift of about 39 decibels, as averaged across all frequencies. Noting that an average threshold shift that is high (e.g., about 25 decibels or higher) is undesirable and considered to be a clinically significant hearing handicap, the average threshold shift of the composition consisting essentially of "ACEMg" is low (e.g., about 15 decibels). The low average threshold shift of the composition consisting essentially of "ACEMg" is significantly less than the average threshold shift of any of the other compositions (each producing threshold shifts of hearing loss that is well over 25 decibels). This result shows that the composition consisting essentially of "ACEMg" performs better than any of the other compositions tested in terms of treating hearing loss.

As shown in FIG. 7, outer hair cell counts reveal reduced sensory cell death in both the whole cochlea and in the trauma region, compared to the saline control, with i) the guinea pig treated with a composition including magnesium and ii) the guinea pig treated with a composition including "ACE". However, the best results were obtained utilizing a composition consisting essentially of "ACEMg". Specifically, treatment with the composition consisting essentially of "ACEMg" results in less than 10% of the outer hair cells in the whole cochlea were missing, and less than 15% of the outer hair cells in the trauma region were missing. It is noted that more than 15% of missing outer hair cells in the whole cochlea and more than 25% of missing outer hair cells in the trauma region is generally undesirable.

Treatment of hearing loss utilizing creatine kinase is also explored. It has been known that exposure to high intensity sound will trigger a decrease in local blood flow of the inner ear, especially at very high sound exposure levels, e.g., at 120 dB to 155 dB. At the same time, metabolic activity will remain elevated well above basal levels. At the very high sound exposure levels, a reduction in cochlear blood flow (CBF) and local vasoconstriction may subject the cochlea to severe hypoperfusion in the presence of high energy demands, leading to further increase(s) in free radical formation. Impaired energy status may then lead to activation of excitatory amino acid receptors, thereby increasing intracellular calcium and the generation of free radicals. These are all potentially damaging to the inner ear.

An initial step in the development of noise trauma may be a depletion of cellular energy stores. It is believed that agents that can buffer cellular energy stores may also be useful for treating hearing loss. An example of such an agent is creatine kinase (as previously mentioned). Creatine kinase is an enzyme involved in regulating energy metabolism in cells with intermittently high and fluctuating energy requirements, including the inner ear. The enzyme catalyzes the transfer of high-energy phosphate from phosphocreatine to Adenosine Di-Phosphate (ADP) to generate Adenosine Tri-Phosphate (ATP).

Several cytoplasmic and mitochondrial isoforms have been identified that, with the substrates creatine and phosphocreatine, constitute an intricate cellular energy buffering and transport system connecting sites of energy production to sites of energy consumption. The compounds that increase cochlear energy reserve may be protected by determining whether or not the oral administration of creatine attenuates noise-inducing hearing loss.

Referring back to FIG. 6, treatment with a composition including creatine results in a threshold shift of about 34 decibels, as averaged across all frequencies, which is less than the threshold shift of the saline control sample and composition including magnesium. However, treatment with a composition including "ACEMg" and creatine did not perform well. For instance, treatment with the composition including "ACEMg" and creatine produced a threshold shift of about 44 decibels, as averaged across all frequencies, which is almost as high as the average threshold shift of the saline control sample. As shown in FIG. 7, outer hair cell counts revealed reduced sensory cell death in both the whole cochlea and in the trauma region, compared to the saline control, with the guinea pig treated with a composition including creatine. Even further reduction in sensory cell death of the outer hair cells in the whole cochlea and in the trauma region occurs with the guinea pig treated with a composition including "ACEMg" and creatine.

Compositions including salicylate are also tested for their efficacy for treating hearing loss. Salicylate is a derivative of salicylic acid that occurs naturally in plants, and serves as a natural immune hormone and preservative. Salicylate acts as a powerful antioxidant inside the body. As shown in FIG. 6, treatment with a composition including "ACEMg" and salicylate results in a threshold shift of hearing loss, as averaged across all frequencies, that is about the same as the threshold shift of hearing loss of a composition including creatine alone. However, treatment with a composition including "ACEMg", creatine, and salicylate also did not perform as well as the composition including "ACEMg" and salicylate. For instance, treatment with the composition including "ACEMg", creatine, and salicylate produced a threshold shift of hearing loss of about 36 decibels, as averaged across all frequencies, whereas treatment of the composition including "ACEMg" and salicylate produced a threshold shift of hearing loss of about 34 decibels, as averaged across all frequencies. As shown in FIG. 7, sensory cell death of the outer hair cells in the whole cochlea and in the trauma region is slightly reduced with the guinea pig treated with the composition including "ACEMg" and salicylate compared to guinea pig treated with the composition including "ACEMg" and creatine. A further slight reduction in the sensory cell death of the outer hair cells in the whole cochlea and in the trauma region occurs with the guinea pig treated with the composition including "ACEMg", creatine, and salicylate compared to the guinea pig treated with "ACEMg" and salicylate.

In view of the results shown in FIGS. 6 and 7, the composition consisting essentially of "ACEMg" performed the best compared to all of the other compositions tested.

The inventive composition that consists essentially of vitamin A, vitamin C, vitamin E, and a vasodilator comprising magnesium, in the biologically effective amounts, provides an additive effect in treating hearing loss that is equal to or greater than a sum of the effect of the individual components. Even more, the inventive composition proves to be effective in treating hearing loss if administered as late as three days after trauma to the inner ear of the mammal. As a result, the composition of the subject invention provides great promise in helping to minimize hearing loss resulting from trauma to inner ears of mammals. Given the high incidence of noise-induced hearing loss in the general population worldwide, there is a great need for the inventive composition in order to minimize socioeconomic effects that persist due to noise-induced hearing loss.

Furthermore, the inventive composition that consists essentially of vitamin A, vitamin C, vitamin E, and a vasodilator comprising magnesium, in the biologically effective amounts, provides an effective treatment for treating side effects of the antibiotic-treatment, including treatment of hearing loss, kidney damage, and loss of balance. In particular, by internally administering the inventive composition in conjunction with administration of the antibiotic, alleviation of side effects of the antibiotic treatment can be accomplished that is both significant and unexpected. Even more, the composition proves to be effective in treating side effects of antibiotic treatment if administered as late as three days after the first dosage of the antibiotic is administered to the mammal. As a result, the inventive composition provide great promise in helping to minimize side effects of antibiotic treatment, especially since there are no negative side effects associated with administration of the composition and since all of the components of the composition are cost-effective, readily available, and long-proven as safe for human treatment.

The invention has been described in an illustrative manner, and it is to be understood that the terminology which has been used is intended to be in the nature of words of description rather than of limitation. Obviously, many modifications and variations of the present invention are possible in light of the above teachings, and the invention may be practiced otherwise than as specifically described.

What is claimed is:

1. A composition to be administered to a mammal for treating hearing loss, the composition consisting essentially of: a biologically effective amount of vitamin A, vitamin E, vitamin C, a vasodilator chosen from magnesium, a magnesium salt and/or magnesium salt complex, and, optionally, a withanolide and/or resveratrol, to provide an additive effect that is equal to or greater than a sum of the effects of the individual components.

2. The composition as set forth in claim 1 wherein said vitamin A is retinol or beta-carotene.

3. The composition as set forth in claim 1 wherein said vitamin A is present in the composition in an amount of at least 830 IU.

4. The composition as set forth in claim 3 wherein said vitamin A is retinol, and wherein said retinol is present in said composition in an amount from 830 IU to 10,000 IU.

5. The composition as set forth in claim 3 wherein said vitamin A is beta-carotene, and wherein said beta-carotene is present in the composition in an amount from 830 IU to 50,000 IU.

6. The composition as set forth in claim 1 wherein said vitamin E is a water-soluble analog of alpha-tocopherol.

7. The composition as set forth in claim 1 wherein said vitamin E is present in said composition in an amount of at least 75 IU.

8. The composition as set forth in claim 1 wherein said vitamin E is present in the composition in an amount from 75 IU to 2,000 IU.

9. The composition as set forth in claim 1 wherein said vitamin C comprises L-ascorbic acid, L-dehydroascorbic acid, and salts thereof.

10. The composition as set forth in claim 1 wherein said vitamin C is present in said composition in an amount of at least 4,000 IU.

11. The composition as set forth in claim 1 wherein said vitamin C is present in an amount from 4,000 IU to 60,000 IU.

12. The composition as set forth in claim 1 wherein said vasodilator is chosen from magnesium sulfate, magnesium citrate, magnesium acetate, magnesium aspartate, magnesium carbonate, magnesium chloride, magnesium fumarate, magnesium gluconate, magnesium glycinate, magnesium hydroxide, magnesium lactate, magnesium oxide, magnesium salicylate, and magnesium stearate.

13. The composition as set forth in claim 1 wherein said magnesium salt is from a hydrobromide salt, a hydrochloride salt, a bisulfate salt, a nitrate salt, an arginate salt, an ascorbate salt, an oxalate salt, a valerate salt, an oleate salt, a palmitate salt, a laurate salt, a borate salt, a benzoate salt, a phosphate salt, a tosylate salt, a maleate salt, a fumarate salt, a succinate salt, a taurate salt, a tartrate salt, a naphthylate salt, a mesylate salt, a glucoheptonate salt, a lactobionate salt, and a laurylsulphonate salt.

14. The composition as set forth in claim 1 wherein said vasodilator is present in said composition in an amount from 50 mg to 450 mg.

15. The composition as set forth in claim 1 wherein said composition comprises said withanolide, and wherein said withanolide is present in said composition in an amount of at least 10 ppm.

16. The composition as set forth in claim 1 said composition comprises said withanolide, and wherein said withanolide is present in an amount from 10 ppm to 1,000 ppm.

17. A compositional system to be administered to a mammal for treating hearing loss, the compositional system comprising: the composition of claim 1 and an antibiotic.

18. The compositional system as set forth in claim 17 wherein said antibiotic is chosen from amikacin, arbekacin, gentamicin, kanamycin, neomycin, netilmicin, paromomycin, rhodostreptomycin, streptomycin, tobramycin, and apramycin, and a glycopeptide antibiotic.

19. The compositional system as set forth in claim 18 wherein said glycopeptide antibiotic is chosen from vancomycin, teicoplanin, telavancin, bleomycin, ramoplanin, and decaplanin.

20. A composition to be administered to a mammal for treating hearing loss, said composition consisting essentially of: at least 830 IU of beta-carotene; at least 75 IU of vitamin E; at least 4,000 IU of vitamin C comprising ascorbic acid; and at least 50 mg of $MgSO_4$.

* * * * *